(12) United States Patent
Deisseroth et al.

(10) Patent No.: US 7,670,838 B2
(45) Date of Patent: Mar. 2, 2010

(54) COUPLING OF EXCITATION AND NEUROGENESIS IN NEURAL STEM/PROGENITOR CELLS

(75) Inventors: Karl Deisseroth, Palo Alto, CA (US); Robert C. Malenka, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 281 days.

(21) Appl. No.: 11/134,720

(22) Filed: May 19, 2005

(65) Prior Publication Data

US 2005/0267011 A1 Dec. 1, 2005

Related U.S. Application Data

(60) Provisional application No. 60/574,281, filed on May 24, 2004.

(51) Int. Cl.
*C12N 5/00* (2006.01)
*C12N 5/02* (2006.01)
*C12N 5/08* (2006.01)

(52) U.S. Cl. .................. 435/377; 435/325; 435/368

(58) Field of Classification Search ............. 435/377, 435/325, 368
See application file for complete search history.

(56) References Cited

U.S. PATENT DOCUMENTS 6,497,872 B1 * 12/2002 Weiss et al. ................. 424/93.1

OTHER PUBLICATIONS

Nacher J, Alonso-Llosa G, Rosell DR, McEwen BS. NMDA receptor antagonist treatment increases the production of new neurons in the aged rat hippocampus. Neurobiol Aging. Mar.-Apr. 2003;24(2):273-84.*
Eisen A, Weber M. Treatment of amyotrophic lateral sclerosis. Drugs Aging. Mar. 1999;14(3):173-96 (abstract only).*
Brinton RD, Wang JM. Preclinical analyses of the therapeutic potential of allopregnanolone to promote neurogenesis in vitro and in vivo in transgenic mouse model of Alzheimer's disease. Curr Alzheimer Res. Feb. 2006; 3(1):11-7 (abstract only).*
Kitayama T, Yoneyama M, Tamaki K, Yoneda Y.Regulation of neuronal differentiation by N-methyl-D-aspartate receptors expressed in neural progenitor cells isolated from adult mouse hippocampus. J Neurosci Res. Jun. 1, 2004;76(5):599-612.*
Deisseroth et al., Signalin G From Synapse to Nucleus: Postsynaptic CREB Phosphorylation During Multiple Forms of Hippocampal Synaptic Plasticity, (1996), Neuron, 16, 89-101.
Deisseroth et al., Translocation of Calmodulin to the Nucleus Supports CREB Phosphorylation in Hippocampal Neurons, (1998), Nature, 392, 198-202.
Deisseroth et al., Signaling From Synapse to Nucleus: The Logic Behind the Mechanisms, (2003), Curr Opin Neurobiol., 13, 354-65.
Monje et al., Irradiation Induces Neural Precursor-Cell Dysfunction, (2002), Nat Med, 8(9), 955.
Palmer et al., The Adult Rat Hippococampus Contains Primordial Neural Stem Cells, (1997), Mol Cell Neurosci, 8, 389-404.
Palmer et al., Fibroblast Growth Factor-2 Activates a Latent Neurogenic Program in Neural Stem Cells From Diverse Regions of the Adult CNS, (1999), J Neurosci, 19, 8487-8497.

* cited by examiner

*Primary Examiner*—Thaian N Ton
(74) *Attorney, Agent, or Firm*—Bozicevic, Field & Francis LLP; Pamela J. Sherwood

(57) ABSTRACT

Coupling of excitation to neurogenesis in proliferating postnatal NPCs is demonstrated in vitro and in vivo. Neurogenesis is potently enhanced by excitatory stimuli, and involves $Ca_v1.2/1.3$ channels and NMDA receptors. These $Ca^{2+}$ influx pathways are located on the proliferating NPCs, allowing them to directly sense and process excitatory stimuli. Excitation increases the fraction of NPC progeny that are neurons, and increases total neuron number. Signaling in this pathway leads to rapid induction of a proneural gene expression pattern involving the bHLH genes HES1, Id2, and NeuroD, and the resulting cells become fully functional neurons defined by neuronal morphology, expression of neuronal structural proteins, expression of neuronal TTX-sensitive voltage gated $Na^+$ channels, and synaptic incorporation into active neural circuits.

13 Claims, 8 Drawing Sheets
(8 of 8 Drawing Sheet(s) Filed in Color)

COUPLING OF EXCITATION AND NEUROGENESIS IN NEURAL STEM/PROGENITOR CELLS

BACKGROUND

Neurogenesis occurs throughout life, particularly in the hippocampus, and the balance of neuronal loss and birth is essential in generating the plasticity necessary for new memory formation. In the adult mammalian hippocampus, production of new neurons is influenced by a variety of environmental and behavioral conditions. Factors that have been described as influencing neurogenesis, include, for example, exercise, diet, environmental stimulation, steroids, electroconvulsive therapy, and antidepressants. These findings have stimulated great interest in determining if hippocampal activity itself meaningfully guides neurogenesis, thereby implementing a novel form of network plasticity at the cellular level that would go beyond the well-known forms of plasticity that occur at the synaptic level. Insertion of new neurons could modulate the capability of the adult hippocampal network to handle storage of new memories or clearance of old memories. Furthermore, linking neurogenesis to neuronal activity might adapt the adult network both to physiological demands and to pathological insults.

The generation of new neurons within the hippocampus is mediated by proliferating neural stem/progenitor cells, which are highly sensitive to local signaling. Stem cells represent the most immature cell necessary for neurogenesis. These cells give rise to more restricted precursors or progenitor cells and ultimately these progenitors differentiate into new functional neurons. These cells produce neurons in response to signals received from surrounding cells as well as humoral signals from circulating hormones, cytokines, and growth factors. Gross alterations in local microenvironments may allow ectopic neurogenesis to occur, or even block essential neurogenesis, leading to deficits in neurogenesis-dependent functions, such as learning and memory.

There are numerous diseases associated with neurodegeneration. For example, Parkinson's disease is associated with a loss of dopaminergic neurons in certain brain regions. Alzheimer's Disease is characterized by the death of nerve cells in regions of the brain involved in language and memory. In addition, aging may be associated with a decrease in synaptic plasticity, which leads to a reduction in memory. Other neurodegenerative diseases include Huntington's chorea and amyotrophic lateral sclerosis (Lou Gehrig's disease). Mild cognitive impairment (MCI) that afflicts millions of Americans over the age of 45, unrelated to frank dementia or Alzheimer's disease, may also be related to neuronal loss.

Trauma is also a cause of neural damage. Traumatic brain injury (TBI) can significantly affect many cognitive, physical, and psychological skills. Physical deficit can include ambulation, balance, coordination, fine motor skills, strength, and endurance. Cognitive deficits of language and communication, information processing, memory, and perceptual skills are common. Brain injury can occur in many other ways, including accidents in which the head strikes an object, insufficient oxygen as occurs during strokes, poisoning, or infection.

Altered neuron number in the brain, in particular within the hippocampus, may also occur during mental illnesses such as depression, anxiety disorders, schizophrenia, and autism. For example, the hippocampus tends to be smaller in humans suffering from depression, anxiety disorders such as PTSD, and schizophrenia, and neuron number may be increased in autism. Furthermore, many clinically efficacious anti-depressant medications enhance neurogenesis in the hippocampus.

There is a need to develop compounds and methods of treatment that prevent the onset, and/or ameliorate the symptoms, of diseases associated with damage, dysfunction, or degeneration of neurons. There is also a need to develop compounds and methods of treatment to improve the regeneration and repair of neurons in the brain. Preferably, the treatment will allow for controlled neurogenesis to replace damaged neurons, or to prevent the loss of neurons. Compounds that prevent or reduce neurodegeneration may be used to prevent a variety of diseases, or may be used to specifically target one disease or brain region.

Publications

Aspects of neurogenesis are disclosed, for example, in Deisseroth et al. (1996) Neuron 16, 89-101; Deisseroth et al. (1998) Nature 392, 198-202; Deisseroth et al. (2003) Curr Opin Neurobiol. 13, 354-65; Monje et al. (2002) Nat Med 5, 5; Palmer et al. (1999) J Neurosci 19, 8487-8497; Palmer et al. (1997) Mol Cell Neurosci 8, 389-404; and U.S. patent application 20020155173.

SUMMARY OF THE INVENTION

Methods are provided for modulating neurogenesis by direct excitation of neural progenitor cells (NPCs). Excitation promotes neurogenesis primarily by acting via NMDA receptors, and high voltage-activated gated $Ca^{2+}$ channels, which are present on the NPCs themselves. In mature neurons, these channels open primarily in response to the depolarization provided by excitatory synaptic inputs. Direct excitation may be achieved through electrical signaling, altering ionic concentrations in the NPC environment, or may be simulated by contacting NPCs with chemical agents that are specific agonists or antagonists of these channels and/or receptors. Excitation through this pathway is shown to increase the neuronal cells produced by NPCs.

In one embodiment of the invention, methods are provided for treating a subject having or being susceptible to a neurological disorder or a neuronal injury. The method entails administering to the subject a prophylactic or therapeutically effective amount of an agent that increases neurogenesis by NPCs. The neuropsychiatric disorders amenable to treatment with the methods include traumatic brain injury, stroke, Parkinson's disease, Huntington's disease, inherited ataxias, motor neuron diseases, Alzheimer's disease, depression, schizophrenia, PTSD, and the like. In other instances it may be desirable to inhibit neurogenesis, through the administration of an inhibitor of the pathways, channels, or genes identified herein.

In another embodiment of the invention, methods are provided for screening drug candidates for effectiveness in increasing the production of neural cells by NPCs. Screening assays may utilize the culture methods of the invention; and/or may be performed using a variety of assays designed to specifically test the effect of a compound on high voltage-activated gated $Ca^{2+}$ channels; and/or NMDA receptors, or components of their downstream signaling pathways which include second messengers such as calcium ions, transcription factors such as Hes1 and Id2, and differentiation factors such as NeuroD. Screening may be used to identify agents that selectively target one isotype or another of these molecular players to improve targeting specificity of the intervention.

In another embodiment of the invention, a software model for information storage using simulated neural networks using a simple layered neural network capable of storing and recalling many patterns of activity is provided. The model provides a means of analyzing the effects of neurogenesis in a network, e.g. in adaptation to different levels of memory storage demands; correlation with activity level on the network; and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
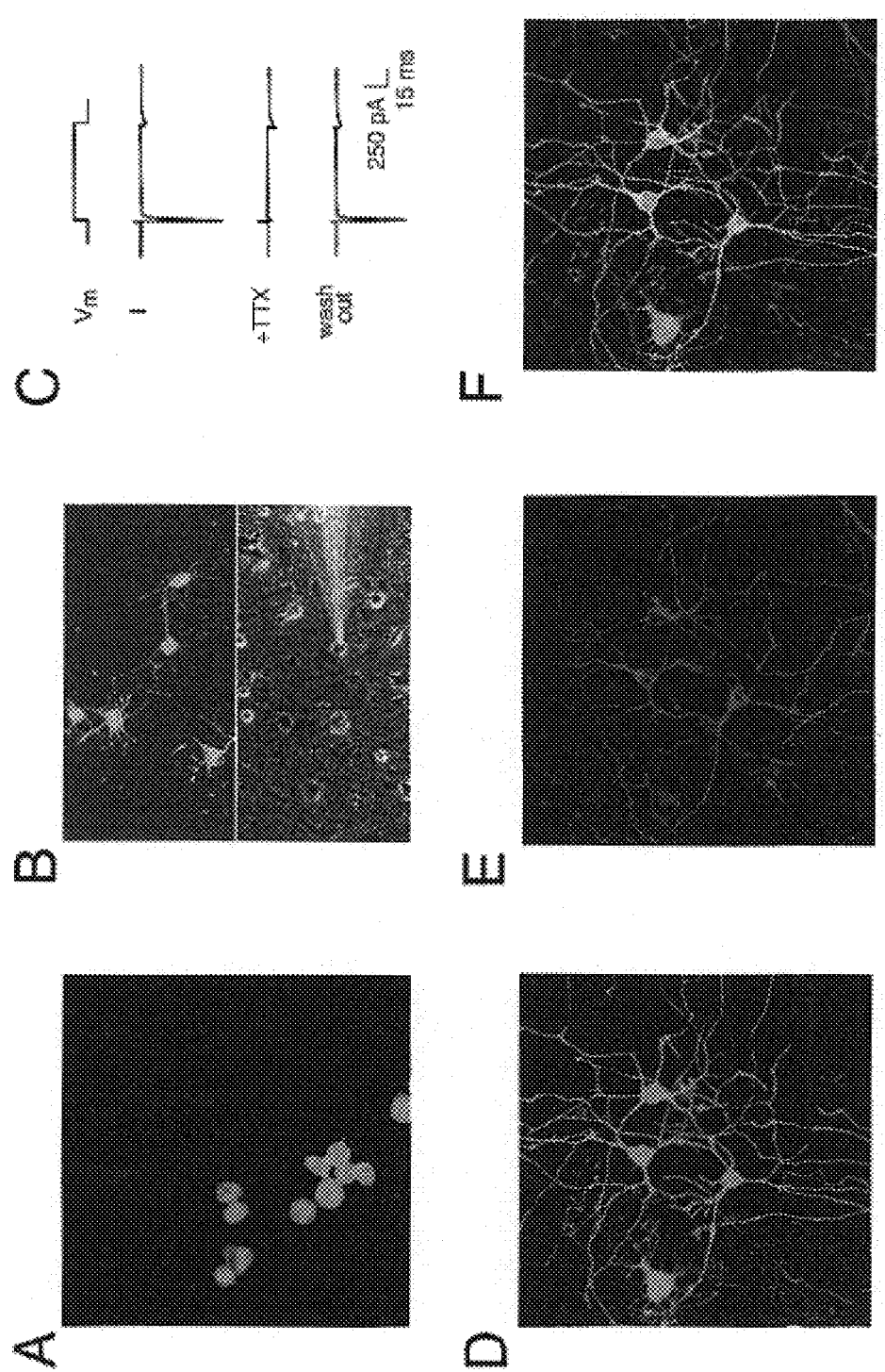
FIG. 1A-1F. In vitro system for studying the relationship of excitation to neurogenesis. A, GFP-labeled adult hippocampal HC37 NPCs in proliferative culture. B, Example of whole-cell patch clamp recording from a differentiated NPC-derived neuron in coculture. HC37 cells were grown with hippocampal neurons and glia in retinoic acid-containing medium permitting neuronal differentiation. C, Example of voltage-activated Na$^+$ current evoked from an NPC-derived neuron. Tetrodotoxin (TTX, 1 μM) reversibly blocked the inward current evoked with a step from −70 mV to −10 mV. D, Morphology of differentiated progeny: GFP expression shown. E, Same field of cells as in D; MAP2ab expression shown. Cells lacking neuronal morphology (the cell on the left; without 2-5 well-defined primary processes) consistently expressed little MAP2ab, while cells with neuronal morphology (the three cells on the right) expressed high levels of MAP2ab. F, Overlay of GFP (green) and MAP2ab (red) expression, with spatial overlap (yellow) signifying the conjunction.

Methods are provided for protecting or treating an individual suffering from adverse effects of deficits in neurogenesis, or in some instances from undesirably active neurogenesis. Excitation promotes neurogenesis; acting via NMDA receptors, and high voltage-activated gated $Ca^{2+}$ channels. These findings have broad implications for a variety of diseases of mentation, mood, cognition or which involve neurodegeneration. Neurogenesis is enhanced by direct excitation through electrical signaling or altering ionicity in the NPC environment; or by contacting NPCs with chemical agents that are specific agonists or antagonists of these channels and/or receptors. Conversely, neurogenesis is inhibited by contacting NPCs with inhibitors or antagonists of these channels and/or receptors.

Neurogenesis. The term neurogenesis refers to the generation of new neurons from proliferating neural stem/progenitor cells. Neurogenesis may take place in vitro, e.g. in the model culture systems described herein, or in vivo. In vivo neurogenesis may arise from naturally occurring NSCs or NPCs; or from transplanted NSCs or NPCs, where the cells may be autologous, allogeneic, etc.

Neural stem cells give rise to more restricted precursors or progenitor cells and ultimately these progenitors differentiate into new functional neurons. The term "neural stem cells" (NSCs) includes "neural progenitor cell," "neuronal progenitor cell," "neural precursor cell," and "neuronal precursor cell" (all referred to herein as NPCs).

Neural stem/progenitor cells have been described in the art, and their use in a variety of therapeutic protocols has been widely discussed, for example, inter alia, in U.S. Pat. No. 6,638,501, Bjornson et al.; U.S. Pat. No. 6,541,255, Snyder et al.; U.S. Pat. No. 6,498,018, Carpenter; U.S. patent application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148 (1):135-46 and Shihabuddin (1999) Mol Med Today. 5(11): 474-80; each herein specifically incorporated by reference.

Neural stem cells are defined by their ability to undergo continuous cellular proliferation, to regenerate exact copies of themselves (self-renew), to generate a large number of regional cellular progeny, and to elaborate new cells in response to injury or disease. Typically, the cells express some of the phenotypic markers that are characteristic of the neural lineage. They also do not usually produce progeny of other embryonic germ layers when cultured by themselves in vitro unless dedifferentiated or reprogrammed in some fashion.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. As such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like.

Neural stem cells can be obtained from embryonic or post-natal, e.g. juvenile, or adult mammalian neural tissue (e.g. mouse and other rodents, and humans and other primates) and can be induced to proliferate in vitro or in vivo using various methods as known in the art. For example, the administration of one or more growth factors can be used to induce the proliferation of multipotent neural stem cells. For the proliferation of multipotent neural stem cells in vitro, neural tissue may be dissociated and the primary cell cultures cultured in a suitable culture medium, including the culture methods described in the examples.

In a culture system of interest for screening methods of the invention, NPCs are cultured on a substrate of hippocampal cells. NPCs may be obtained from established cell lines, or may be isolated from hippocampi by dissociation. The population may be enriched for neural progenitors by density separation, e.g. percoll gradient, etc. The cells are optionally labeled by infection with replication deficient retrovirus encoding a detectable marker, e.g. green fluorescent protein, and the like.

Neurogenesis is quantitated by culturing the NPC on a substrate of primary hippocampal cell cultures in the presence of mitogen, e.g. VEGF, PDGF, etc. and then tapering the mitogen in medium that permits neuronal differentiation. The hippocampal substrate may be living, or may be ethanol-fixed and extensively washed.

In vivo, neural stem cells (NSCs) are located within the ependymal and/or subventricular zone (SVZ) lining the lateral ventricle and in the dentate gyrus of the hippocampus formation. Additional locations of NSC within the post-natal CNS are also possible. Asymmetric division of NSC maintains their number, while generating a population of rapidly dividing precursor or progenitor cells. The progenitors respond to a range of cues that dictate the extent of their proliferation and their fate, both in terms of the cell type that they differentiate into and the position that they ultimately take up in the brain.

The NSCs of the ventricular system in the adult are likely counterparts of the embryonic ventricular zone stem cells lining the neural tube. NSCs persist in the adult lateral ventricle wall (LVW), generating neuronal progenitors which migrate down the rostral migratory stream to the olfactory bulb, where they differentiate into granule cells and periglomerular neurons. Substantial neuronal death occurs in the olfactory bulb generating a need for continuous replacement of lost neurons, a need satisfied by the migrating progenitors derived from the LVW. Lost neurons from other brain regions may also be replaced by progenitors from the LVW that differentiate into the lost neuron phenotype.

By "promoting neurogenesis" as used herein, it is meant that the number of neurons in a system is increased, and/or the fraction of NPC progeny having a neuronal phenotype is increased. Neurogenesis is "modulated" by the methods of the invention, which may comprise increasing, or promoting neurogenesis, or inhibiting neurogenesis. By inhibiting neurogenesis, it is meant that the number of neurons is decreased, or the fraction of NPC progeny having a neuronal phenotype is decreased. Generally such an increase or decrease is relative, as compared to a comparable situation in the absence of the treatment. For example, in a condition where there is a short term burst of undesirable neurogenesis, the methods of the invention may prevent such an increase, and result in stable numbers of neurons.

High voltage gated $Ca^{2+}$ channel. The $Ca^{2+}$ channels found to activate neurogenesis include the $Ca_v1.2/1.3$ channel, which may also be referred to as the alpha-1C and D channels. This channel is present on neural progenitor cells, and in mature neurons is activated by synaptic signaling. Voltage-sensitive $Ca^{2+}$ channels play an important role in regulating hormone and neurotransmitter release, muscle contraction, and a large number of other cellular functions. The voltage-sensitive $Ca^{2+}$ channels are multisubunit proteins. The alpha-1 and beta subunits are members of gene families; cDNAs encoding several structurally related alpha-1 subunits and beta subunits have been reported. On the basis of their kinetics and pharmacology, 4 types of $Ca^{2+}$ currents have been described. The $Ca^{2+}$ channel activity associated with the skeletal muscle, heart, and neuroendocrine/brain alpha-1 subunit isoforms is inhibited by dihydropyridine drugs, indicating that these represent L-type currents. The sequence of the alpha 1 D subunit may be accessed at Genbank, number M76558, and is also described by Williams et al. (1992) Neuron 8 (1):71-84. The sequence of the alpha 1C subunit may be accessed at Genbank, number L29534, and is also described by Klockner et al. (1997) Am. J. Physiol. 272 (3 Pt 2), H1372-H1381.

The mode of calcium entry into a neuron plays a key role in determining which signaling pathways are activated and thus specifies a cellular response to calcium. Calcium influx through L-type voltage-activated channels (LTCs) is particularly effective at activating transcription factors such as CREB and MEF2. An isoleucine-glutamine (IQ) motif in the C terminus of the LTC that binds calcium-calmodulin is critical for conveying the calcium signaling to the nucleus. Calcium-calmodulin binding to the LTC was necessary for activation of the Ras/mitogen-activated protein kinase (MAPK) pathway, which conveys local calcium signals from the mouth of the LTC to the nucleus. Calmodulin functions as a local calcium sensor at the mouth of the LTC that activates the MAPK pathway and leads to the stimulation of genes that are essential for neuronal survival and plasticity.

Certain functions of $Ca_v1.2/1.3$ channels can also be served by NMDA receptors; the two channel types often provide overlapping effects, likely due to a common ability to recruit calmodulin signaling. NMDA receptors are a subclass of excitatory, ionotropic L-glutamate neurotransmitter receptors. These ion channels allow ions to flow into a neuron upon depolarization of the postsynaptic membrane, and when the receptor is activated by glutamate, aspartate, or an agonist drug. They are heteromeric, integral membrane proteins formed by the assembly of the obligatory NR1 subunit together with modulatory NR2 subunits. The NRI subunit is the glycine binding subunit and exists as 8 splice variants of a single gene. The glutamate binding subunit is the NR2 subunit, which is generated as the product of four distinct genes, and provides most of the structural basis for heterogeneity in NMDA receptors. In the hippocampus and cerebral cortex, the active subunit NMDAR1 is associated with 1 of 2 regulatory epsilon subunits: NMDAR2A or NMDAR2B and NR3. Unless otherwise specified, the term "NMDA-R" or "NMDA receptor" as used herein refers to an NMDA receptor molecule that has an NR1 subunit and at least one NR2A or NR2B subunit.

An exemplary NR1 subunit is the human NMDAR1 polypeptide. The sequence of the polypeptide and corresponding nucleic acid may be obtained at Genbank, accession number L05666, and is published in Planells-Cases et al. (1993) P.N.A.S. 90(11):5057-5061. An exemplary NR2 subunit is the human NMDAR2A polypeptide. The sequence of the polypeptide and corresponding nucleic acid may be obtained at Genbank, accession number U09002, and is published in Foldes et al. (1994) Biochim. Biophys. Acta 1223 (1):155-159. Another NR2 subunit is the human NMDAR2B polypeptide. The sequence of the polypeptide and corresponding nucleic acid may be obtained at Genbank, accession number U11287, and is published in Adams et al. (1995) Biochim. Biophys. Acta 1260 (1):105-108.

As used herein, an "agonist" is a molecule which, when interacting with, (for example binding to) a target protein such as the $Ca_v1.2/1.3$ channel or NMDA-R, increases or prolongs the amount or duration of the effect of the biological activity of the target protein. Agonists of channels are molecules that activate the channel. Agonists are preferably selective for the target protein, e.g. by activating the $Ca_v1.2/1.3$ channel but not other ion channels. Agonists of these molecules are known in the art. For example, $Ca_v1.2/1.3$ channel agonists include FPL 64176 and BAY K-8644\ ... NMDA-R agonists include GlyT1 inhibitor N[3-(4'-fluorophenyl)-3-(4'-phenylphenoxy)propyl]sarcosine (NFPS); NM DA; (R)-(+)-HA-966; glycine; D-serine; (RS)-(Tetrazol-5-yl)glycine, and trans-ACBD.

By contrast, the term "antagonist," as used herein, refers to a molecule which, when interacting with, (for example binding to) a target protein such as the $Ca_v1.2/1.3$ channel or NMDA-R decreases the amount or the duration of the effect of the biological activity. Antagonists of these molecules are known in the art. For example, $Ca_v1.2/1.3$ channel antagonists include diltiazem, verapamil, nifedipine, nimodipine, and dimemorfan (3-methyl-N-methylmorphinan); etc. NMDA-R antagonists include D-AP5; MK801, memantine, CGP 39551; SDZ 220-581; CGP 78608 hydrochloride; and 5,7-Dichlorokynurenic acid.

Agonists and antagonists may include proteins, nucleic acids, carbohydrates, antibodies, or any other molecules that decrease the effect of a protein. Unless otherwise specified, the term "agonist" can be used interchangeably with "activator", and the term "antagonist" can be used interchangeably with "inhibitor".

The term "analog" is used herein to refer to a molecule that structurally resembles a molecule of interest but which has been modified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry.

In addition to chemical modulation, $Ca_v1.2/1.3$ channels are activated by electrical signaling. Such signaling may include altering ionicity of the environment, or direct electrical excitation, for example with electroconvusive therapy (ECT). In a preferred method, the excitation is localized to regions of the brain, containing NPCS, e.g. ventricular regions, hippocampus, etc. This could be done with focal stimulation of the brain, e.g. with existing techniques such as transcranial magnetic stimulation (TMS), deep brain stimulation (DBS), vagal nerve stimulation (VNS) or with pharmacological therapies known to target certain brain regions.

For example, methods stimulating neurogenesis may utilize modified electroconvulsive therapy. Typically, a patient undergoing ECT is administered an average of about 6-12 ECT treatments at a frequency of about 2-3 ECT treatments per week. ECT treatment comprises the steps of administration of stimulus, seizure, and recovery, and may be performed under anesthesia, anesthetics, and muscle depolarizing agents to induce paralysis and prevent injury during the seizure. Any device designed for ECT may be used to administer the electrical stimulus, e.g., specially designed machines that create a bidirectional square wave stimulus train up to 8 seconds in length.

Modulating neurogenesis through direct excitation of NPCs or simulation of excitation by administering compounds that act on high voltage gated calcium channels or NMDA receptors is used to promote an improved outcome from ischemic cerebral injury, or other neuronal injury, by inducing neurogenesis and cellular changes that promote functional improvement. The methods are also used to enhance neurogenesis in patients suffering from neurodegenerative disorders. In many instances the individual will be human, however treatment of other mammals is also contemplated, for research purposes, e.g. mice, rats, etc., and/or for veterinary purposes, e.g. horses, dogs, cats, cows, monkeys, etc.

Patients suffer neurological and functional deficits after stroke, CNS injury, and neuropsychiatric/neurodegenerative disease. These findings provide a means to enhance brain compensatory mechanisms to improve function after CNS damage or degeneration. The induction of neurons and cellular changes induced by promoting neurogenesis, e.g. withexcitation-neurogenesis coupling, will promote functional improvement after stroke, injury, aging, neuropsychiatric and neurodegenerative disease. This approach can also provide benefit to patients suffering from other neurological diseases including Alzheimer's disease, Parkinson's disease, Huntington's disease, depression, schizophrenia, PTSD, autism, bipolar disorder, etc. Diseases in which defects in neurogenesis are implicated also include Lewy Body dementia, Frontotemporal dementia/Pick's disease, AIDS dementia complex, dementia puligistica and chronic cognitive dysfunction following head trauma, prion-associated dementia such as Creutzfeldt-Jacob disease, cognitive dysfunction following chronic seizure disorders or an episode of, status epilepticus, cognitive dysfunction following encephalitis or meningitis, amyotrophic lateral sclerosis (ALS)/parkinsonian/dementia complex of Guam.

By "neurological" or "cognitive" function it is meant that the neural growth in the brain enhances the patient's ability to think, function, etc. Humans treated by the methods of the invention have increased production of brain cells that facilitate improved cognitive, memory, and motor function as well as improved mood, thought process, or anxiety regulation.

In one embodiment, the region of increased neurogenesis is within the subventricular zone (SVZ). In another embodiment, the region of increased neurogenesis is within the hippocampus. In another embodiment, the region of increased neurogenesis is within the cortex, striatum, substantia nigra, or other brain region. In another embodiment, the region of increased neurogenesis results from migration of newly divided neurons within the brain, or transplantation of NPC, which may be autologous or allogeneic. The newly divided neurons may migrate to the corpus callosum, striatum, cortex, septum, basal ganglion, nucleus basalis, etc. The amount of increased neurogenesis may comprise at least a measurable increase relative to a control lacking such treatment, for example at least a 10% increase, at least a 20% increase, at least a 50% increase, or more.

The similarities between neural stem cells in the central and peripheral nervous system also indicate that these methods are useful in augmenting neural tissue repair in the peripheral nervous system. Such diseases or injury may include nerve injury due to trauma, surgery, cancer, or immune disease such as multiple sclerosis, ALS, Parkinsons's disease, or other motor neuron disease where endogenous or grafted progenitor/stem cells are influenced by immune mechanisms.

The excitation and/or compounds of the present invention are administered at a dosage that enhances neurogenesis while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials.

Therapeutic agents, e.g. agonists or antagonists as described above can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. an NSAID such as indomethacin may be taken for extended periods of time on a daily or semi-daily basis, while more selective agents, such as antagonists of MCP-1, may be administered for more defined time courses, e.g. one, two three or more days, one or more weeks, one or more months, etc., taken daily, semi-daily, semi-weekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In one aspect of the invention, candidate agents are screened for the ability to modulate neurogenesis. Such compound screening may be performed using an in vitro model, a genetically altered cell or animal, or purified protein, particularly NMDA-R and/or high voltage gated $Ca^{2+}$ channels. A wide variety of assays may be used for this purpose. In one embodiment, compounds that are active in binding assays with the channel proteins, or are predicted to be antagonists or agonists of the channels, or activators or inhibitors of specific downstream signaling molecules, transcription factors, or genes, are then tested in an in vitro culture system, where NPCs are present on a fixed hippocampal substrate, as described above.

For example, candidate agents may be identified by known pharmacology, by structure analysis, by rational drug design using computer based modeling, by binding assays, and the like. Such candidate compounds are used to contact NPCs in an environment permissive for neurogenesis, where living cells other than NPCs are substantially absent in order to provide for a controlled environment. Such compounds may be further tested in an in vivo model for enhanced neurogenesis, or in conventional in vitro models.

The term "agent" as used herein describes any molecule, e.g. protein or pharmaceutical, with the capability of modulating neurogenesis by acting through excitation pathways of neural progenitor cells. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on neurogenesis. The animal models utilized in validation studies generally are mammals. Specific examples of suitable animals include, but are not limited to, primates, mice, and rats.

Neuronal Network Models

A software model for information storage using simulated neural networks using a simple layered neural network capable of storing and recalling many patterns of activity is provided. The model provides a means of analyzing the effects of neurogenesis in a network, e.g. in adaptation to different levels of memory storage demands; correlation with activity level on the network; and the like.

The model may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a graphical representation of the system and/or an interface for querying the model. Such data may be used for a variety of purposes, such as drug discovery, analysis of interactions between cells, and the like.

Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language.

Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Key characteristics of the model network are described herein. The aim of the model is to explore the effects that neuron insertion could have on a memory-storage neural network (and not to precisely mimic a particular preparation, although key parallels to hippocampal functioning are included). The model is a simple layered form of an associative memory neural networks (Graham and Willshaw (1999) Neural Comput. 11, 117-137; Hopfield and Tank, (1986) Science 233, 625-633; McClelland and Rumelhart, (1985) J. Exp. Psychol. Gen. 114, 159-197; Sejnowski (1999) Neuron 24, 773-776; Hopfield (1982) Proc. Natl. Acad. Sci. USA 79, 2554-2558; Meir and Domany (1987) Physical Review Letters 59, 359-362). A "memory" is assumed to be a particular pattern of activity in an assembly of neurons. In this simple implementation, some neurons are active or ON, and some are inactive or OFF, for example, in a certain memory "A." The same assembly of neurons can take on different patterns of activity; in another memory, "B," a different subset of neurons will be ON. Some neurons will be ON in both memories, some will be OFF in both, and some will be ON in one and OFF in another. Stated simply, the neurons have binary activation values $\xi=0$ (OFF) or 1 (ON) in different memories. As in the hippocampus, ON neurons are sparse; here, the fraction of active neurons in any memory (defined as the sparsity $\alpha$)=0.02.

The memory recall function of the network comes about in the following way. When we partially present a memory, say "A," to a minority subset of the neurons ("cueing the memory" by setting the activity values of ON or OFF in this subset of neurons to those values in memory "A"), the entire rest of the network (hitherto left with unset activity values) will find its way to all the correct activity values for that memory "A". The network achieves this memory recall feat upon being cued by making use of information stored in its "synapses," or the interconnections between the neurons. The network is layered, like the hippocampus, and is set up synaptically in three layers (Meir and Domany, 1987). Each neuron in layer 1 has outgoing synapses, or functional connections, to each neuron in layer 2. Each neuron in layer 2 has outgoing connections to each neuron in layer 3. There are no backward (backpropagating) or lateral (recurrent) connections, and the synapses are excitatory and asymmetric just as in the main hippocampal pathways, with clearly defined presynaptic and postsynaptic partners at the synapse (Meir and Domany, 1987). Thus, information flows "forward" through the three layers.

The memory recall feat can be achieved simply by setting the "strength" of the synapses in a well-studied and biologically plausible way, using associative or Hebbian (Sejnowski, 1999) synaptic plasticity rules like those used in the hippocampus. Simply put, the more memories in which two given neurons are both active, the stronger is the excitatory synaptic connection between them. Therefore, the synaptic strength (or "weight") J between any two connected neurons i and j (e.g., the $3^{rd}$ neuron in layer 1 and the $104^{th}$ neuron in layer 2) is set to $J_{ij}=\Sigma(\xi_3 \times \xi_{104})$, summed over all of the stored memories (A, B, . . . ).

The synaptic strengths then come into play during memory recall in the following manner. The network is "cued" to recall a particular memory, e.g., "A," by receiving the activation values in layer 1, set to their correct values for memory "A." Activity is then propagated through the network to layer 2, and subsequently to the output layer 3, as the network attempts to reconstruct the full memory. For example, a given cell j in layer 2 is determined to be active in a reconstructed memory if the incoming activity from layer 1, $\Sigma(\xi_i \times J_{ij})$ summed over all presynaptic layer 1 neurons i into that layer 2 cell j, exceeds a threshold $\theta_j=\alpha \times n$, where n is the total number of neurons in layer 1 and a is the sparsity, as in, the Willshaw model (Willshaw et al. (1969) Nature 222, 960-962). Similarly, activity is then propagated from the second to the third layer, and efficacy of memory recall is judged by similarity of this output layer activity pattern compared with the actual stored memory. Faulty performance is simply quantified as the Hamming distance, defined as the number of output units at which the actual output pattern differs from the learned one. Highly used networks gradually begin to display "noisy" or unreliable recall, as individual synapses attempt to satisfy the requirements of too many memories. This simple and biologically plausible mechanism is extremely effective at storing and recalling memories. For example, a three-layered network with 500 neurons per layer was able to effectively store 500 or more memories and recall them with virtually error-free performance. Although the neurons are simple threshold elements and the network does not attempt to recapitulate hippocampal dynamics, the output layer activity pattern can be readily conceived of as a stable equilibrium of neuronal activity (according to some theories, analogous to the brain state during active remembering), with neurons therein capable of persistent activity or participating in simple recurrent connections.

A strength of this model is that no detailed assumptions about wiring or dynamics were made, as little is known about the functional relevance of these parameters to how information is actually stored in the brain. The simplicity could also be viewed as a disadvantage. However, the central idea is not to "model the hippocampus" but rather to use a layered memory network to gain insight into the effects of neurogenesis on memory recall performance. Do small changes in neurogenesis have large effects on network performance? Are there pronounced effects on both memory degradation and memory storage? Important questions regarding activity-dependent neurogenesis can also be addressed, for example, do the effects of neurogenesis depend upon how active the network has been and how many memories have been stored, and does neurogenesis allow the network to adapt to different levels of memory storage demands?

The model easily allows these questions to be addressed with simulation of neurogenesis at a single internal layer, layer 2 (corresponding to the apparent limitation of adult neurogenesis to the dentate gyrus layer in mammalian hippocampus in nonpathological situations). Neurogenesis is implemented with balanced cell turnover (as thought to occur in vivo in the dentate gyrus; steady addition of new neurons was balanced by steady loss of neurons, keeping network size unchanged), and for cell death, neurons were selected randomly. As newborn neurons must make functional connections in order to learn, new neurons in the model were allowed full connectivity to the presynaptic and postsynaptic layers after being born and were allowed to learn subsequent patterns like the other neurons.

With regard to linking the modeling to our experimental findings, we presume that biological networks which have been actively storing many memories have also been more "active" in the physiological sense, and that this activity may be sensed by cells in the network. This model arises from the conceptualization of a highly active hippocampus as an excitatory environment for cells. In systems terms, if an animal is in a salient and contextually rich habitat, its hippocampus needs to be involved in the storage of many patterns. Substantial glutamatergic activity will pass through the hippocampus and may be sensed over time by the embedded progenitor cells. While the quantitative relationship between real stored memories and locally sensed excitation (e.g., ambient glutamate concentration) is not known, presumably, the more patterns being stored, the more the level of local excitation over time. In this model, then, higher levels of pattern storage correspond to, on average, a more excitatory environment for the progenitors.

With regard to persistence of old memories formed prior to neurogenesis, we found that memory loss/clearance is accelerated by the presence of balanced neurogenesis and cell death. With regard to new memory storage, a relatively quiet network with few stored memories (corresponding to little hippocampal excitatory activity) does almost as well whether or not neurogenesis happens. However, it is clear that a highly active network benefits greatly from neurogenesis. And within these extremes, a monotonically increasing relationship may be seen between extent of excitation and extent of benefit from neurogenesis.

Figure 8:
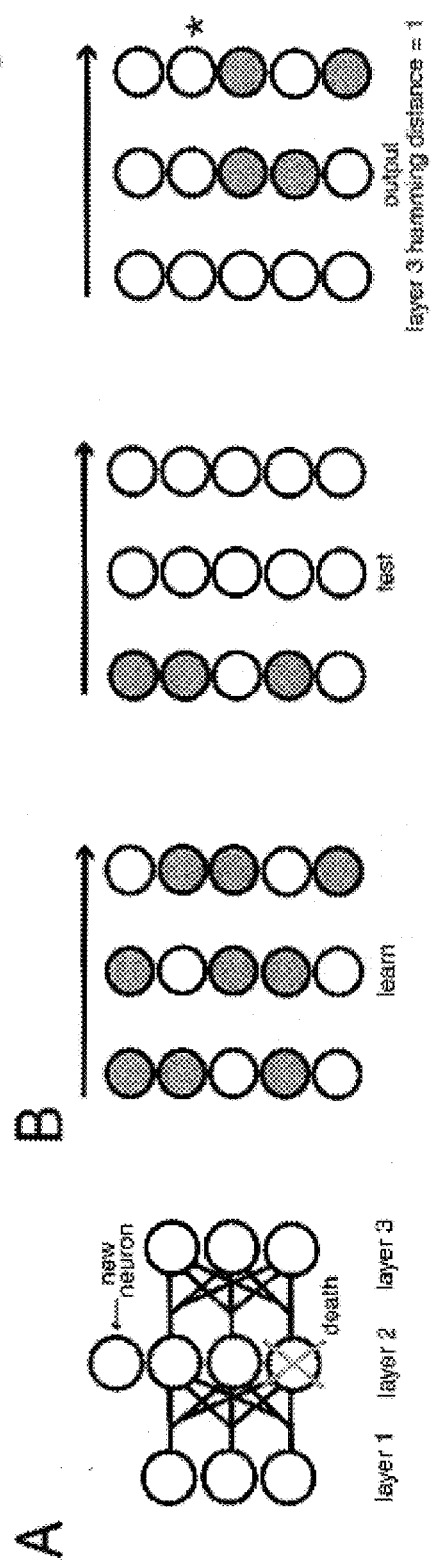
FIG. 8A-8E. Functional consequences of excitation-neurogenesis coupling. A, Diagram of modified associative neural network based on the Willshaw model (Graham and Willshaw (1999) Neural Comput 11, 117-137), with simple parallels to hippocampal processing. Key characteristics are 3-layered structure, feedforward connectivity, sparse representations, and memory storage capability via use of Hebbian synapses (see Experimental Procedures). B, Memories are presented to the input layer (layer 1), processed by the middle layer (layer 2, where neurogenesis is also allowed to occur), and performance assessed at the output layer (layer 3). Performance is quantified as the Hamming distance, defined as the number of output units at which the actual output pattern differs from the learned one. Note the output layer neuron that is incorrectly inactive (*), which would lead to a Hamming distance score of 1. C, Memory loss/clearance caused by cell turnover (balanced neurogenesis and cell death at the hidden layer only; this corresponds to the apparent limitation of adult neurogenesis to the dentate gyrus layer in mammalian hippocampus in nonpathological situations). Older memories are gradually degraded and lost (seen as increased Hamming distance) as the network stores new memories with the Hebb rule. Although even without turnover (stable case) old memories are increasingly lost as new memories are stored, memory loss/clearance is accelerated by the presence of balanced neurogenesis and cell death (neurogenesis case). Here each unit of "time post-learning" corresponds to the learning of 50 new memories; significant degradation of old memories seen even in the stable case begins to be apparent after time=6 corresponding to 700 stored patterns in a network of 500 neurons per layer. D, Marked advantage in storing new memories by allowing neurogenesis/turnover to occur in an excitation-induced manner. High-activity networks involved in high rates of pattern storage increasingly (and monotonically) benefit from turnover. New neurons are better suited to handle incoming memories because of their lack of synaptic involvement in old memories. Network activity level is measured again in units of 50 stored patterns, with higher levels of pattern storage corresponding to more active networks; 500 stored patterns correspond to activity level 1 and 750 stored patterns to activity level 6. Mean values shown in bar plots represent Hamming distances averaged over all stored patterns. E, Experimentally determined neurogenesis increases as a monotonic function of extracellular $[Ca^{2+}]$. Steady depolarization was provided in the presence of 20 mM $K^+$, and varying $[Ca^{2+}]_o$; mean data from 3 independent experiments shown performed in adult NPCs plated on fixed hippocampal substrate.

Critically, this relationship corresponds qualitatively to the experimentally determined monotonically increasing $Ca^{2+}$ dose-response of neurogenesis shown in FIG. 8E. Therefore, this model may be used to simulate optimal levels of neurogenesis and may be helpful in the drug screening or behavioral testing phases of a research or clinical program targeting neurogenesis. Since neurogenesis may accelerate clearance of old memories, this model suggests that it will be particularly advantageous for hippocampal networks to undergo neurogenesis only as needed, and we propose that this can be accomplished by linking neurogenesis to the extent of excitatory activity within the network.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

In vitro system for studying the relationship of excitation to neurogenesis. Although in vivo approaches are clearly important, it is difficult to precisely control and measure activity levels in vivo in a rigorous fashion. Furthermore, it is difficult in vivo to determine which cell type(s) directly sense any changes in activity, much less elucidate the detailed molecular mechanisms responsible. Therefore, to directly determine the neurogenic effects of activity on proliferating post-natal NPCs (excitation-neurogenesis coupling), it was necessary to begin with a reduced in vitro system to provide uniform proliferative conditions, defined excitation and differentiation stimuli, and full physiological characterization of the resulting differentiated cells.

To examine stem/progenitor cell behavior in the presence of mature neurons and glia, green fluorescent protein (GFP)-labeled adult rat hippocampal NPCs (Palmer et al. (1997) Mol Cell Neurosci 8, 389-404) were used. To model the native cell population, we used well-characterized low passage cultures of proliferating cells isolated directly from adult rat hippocampus (FIG. 1A). These cells have been shown to retain stem cell phenotypes in vitro and behave identically to endogenous NPCs when implanted into the intact hippocampus, participating normally in hippocampal neurogenesis.

The fraction of neurons produced from proliferating precursors is substantial at baseline (~50-80%) in the hippocampus of behaving adult rodents. We therefore used baseline in vitro conditions that favor neuronal differentiation. Using established techniques, we plated the proliferating NPCs (FIG. 1A) onto primary hippocampal cultures (Song et al. (2002) Nature 417, 39-44) followed by mitogen taper in medium that permits neuronal differentiation (see Experimental Procedures). After 14 days, ~24% of the cells had differentiated into neurons, expressing the neuronal somatodendritic protein MAP2ab. Neuronal tetrodotoxin (TTX)-sensitive voltage-gated $Na^+$ currents were also expressed, as determined by whole-cell patch clamp (FIG. 1B, 1C). Validating use of MAP2ab as a neuronal marker, the cells that displayed typical mature neuronal morphology (2-5 well-defined primary processes) consistently expressed far greater MAP2ab expression than other cells (3.86±0.28-fold increased MAP2ab intensity measured in confocal sections; illustrated in FIG. 1D-F).

Figure 2:
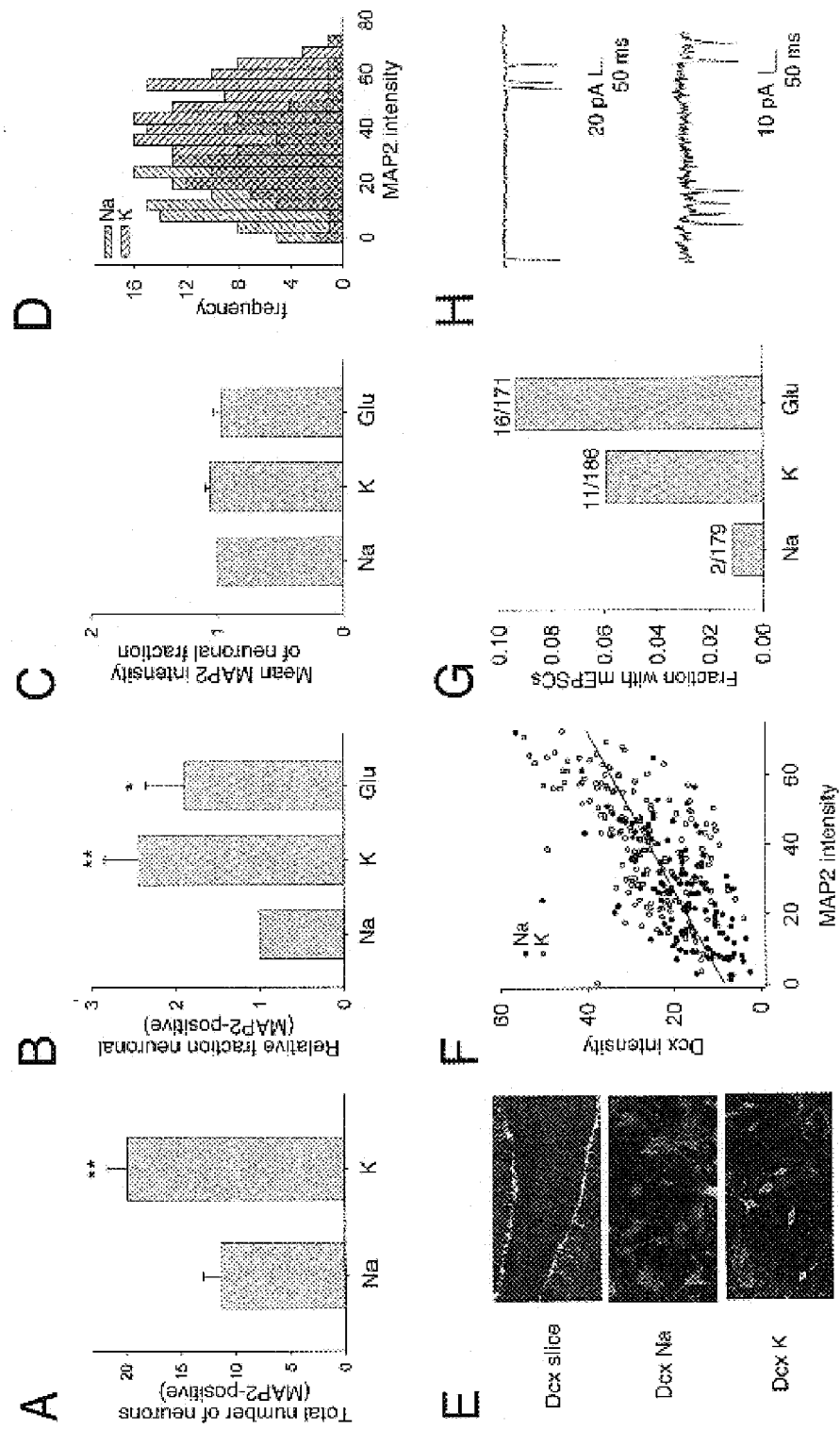
FIG. 2A-2H. Excitation promotes neurogenesis from adult NPCs. A, Depolarization (K) elevated the total neuron number in 10 randomly selected 40× microscope fields by comparison with control (Na) conditions (n=12 independent experiments; p<0.01 by two-tailed t-test). Single asterisk indicates p<0.05; double asterisk indicates p<0.01 here and in subsequent figures. B, Depolarization (K) elevated the fraction of neurons among the NPC progeny (n=12 independent experiments; p<0.01). The fraction of GFP+ cells that were MAP2ab+ is normalized to the fraction found in the Na condition. (The mean neuronal fraction in this control condition across all experiments was 24%.) Excitatory neurotransmitter application (Glu; n=6 independent experiments; p<0.05) also promoted neurogenesis. C, Summary data on extent of single-cell neuronal differentiation in control and excitation conditions as measured by MAP2ab expression level. There was no effect of either stimulus on the mean MAP2ab intensity in the resulting neuronal progeny (p=0.21 for K, p=0.40 for Glu) or in the non-neuronal progeny, indicating that activity increases neuron production rather than extent of neuronal differentiation. Likewise in those (neuronal) cells with TTX-sensitive voltage-gated sodium channel currents, current density was not altered by depolarization. D, Excitation increases neurogenesis, not extent of neuronal differentiation, in individual cells. Shown is MAP2ab intensity vs. frequency histogram of cells in control (Na) or depolarized (K) conditions from a representative experiment. Excitatory activity did not simply promote progression through differentiation after fate commitment, as depolarization increased the proportion of cells expressing high levels of MAP2ab without generating cells that expressed MAP2ab at unusually high levels (histogram). E, Analysis of the neuronal marker Doublecortin (Dcx) also revealed a marked excitation-dependent increase. Top: Dcx staining in adult rat dentate gyrus, demonstrating that only young neurons express this early marker, namely those neurons still lining the subgranular zone and sending processes into the granule cell layer (bracket). Middle: Dcx staining in vitro, in the control (Na) condition; conducted under the same experimental conditions as the MAP2ab assay. Bottom: Dcx staining in vitro, in the excitation (K) condition. F, The excitation-induced increases in MAP2ab and Dcx, two structurally and functionally distinct neuronal proteins, are correlated at the single-cell level (n=304; $r^2$=0.4654; p<0.0001), supporting the identification of these cells as neurons. G, Excitation increased the fraction of cells with functional excitatory synapses as defined by the occurrence of miniature EPSCs. H, Sample mEPSCs from the control (Na) condition (upper trace) and following glutamate stimulation (lower trace).

Excitation promotes neurogenesis from adult NPCs. We next investigated the impact of excitation on neurogenesis by applying modest depolarizing levels of extracellular potassium (20 mM) synchronously with the initiation of mitogen taper (termed day 1). This manipulation mimics the effects of stably increased activity as would occur in an active neural network. We observed an increase in neuron production under these conditions (measured by MAP2ab staining as in FIG. 1)

compared to the non-depolarizing control condition in which equivalent sodium was added as an osmotic control (FIG. 2A).

Figure 6:
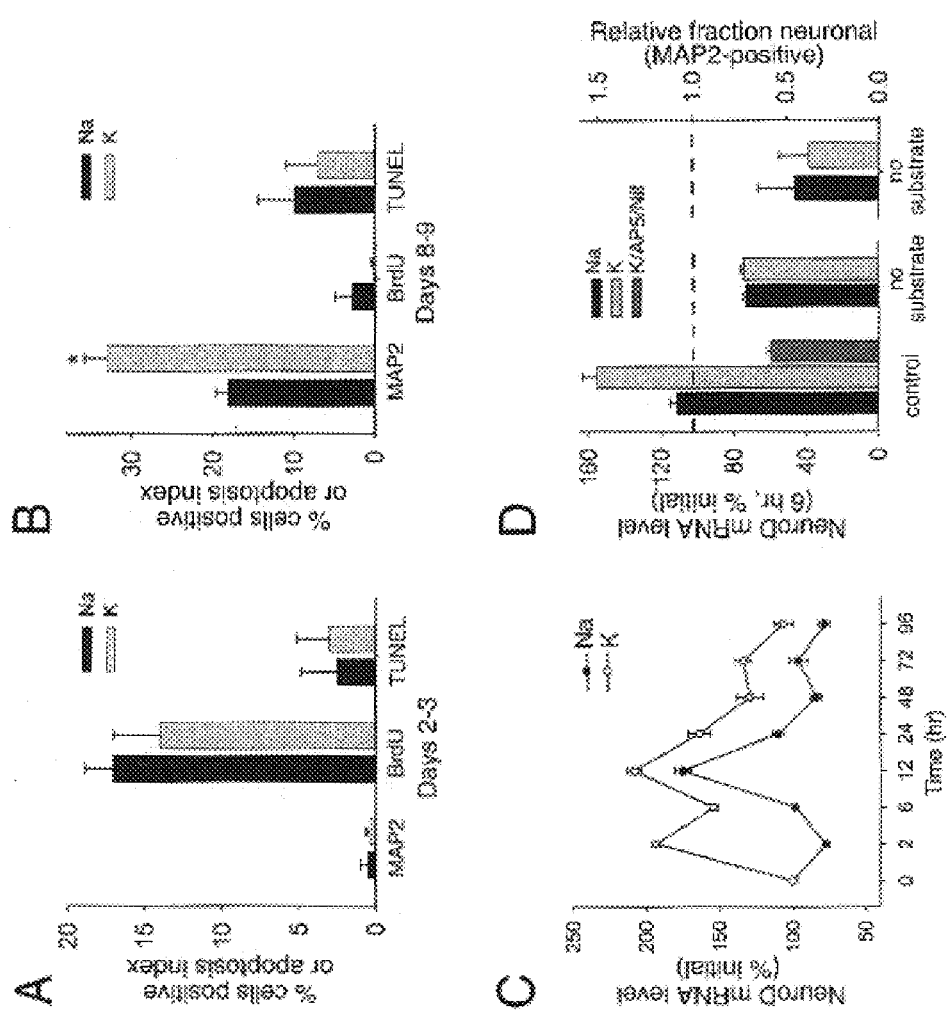
FIG. 6A-6D. Excitation acts to induce a proneural response in proliferating NPCs. A, Assessment of proliferation, survival, and differentiation during days 2 and 3 (average) in excitation or control conditions; as before, excitation begins on day 1. Mean of 3 independent experiments in pure NPCs growing on fixed substrate. Proliferation was measured as % BrdU+ after a brief 2 hr BrdU labeling period and immediate fixation; values were d1 (day of excitation onset): Na 24.4, K 29.1; d2/3: Na 17.1, K 14.3; d4/5: Na 12.1, K 11.8; d6/7: Na 9.6, K 7.5; d8/9: Na 2.8, K 0.2. Apoptosis index is defined as the mean total TUNEL+ cells observed per 20 random fields; values were d1: Na 4.5, K 4.2; d2/3: Na 2.5, K 3.0; d4/5: Na 12.3, K 8.3; d6/7: Na 12.1, K 15.7; d8/9: Na 10.4, K 7.0. Total cell counts from 20 random fields were d1: Na 65.7, K 69.3; d2/3: Na 159.5, K 154.0; d4/5: Na 209.0, K 196.5; d6/7: Na 179.5, K 142; d8/9: Na 40.0, K 51.0. None of these values were significantly altered by excitation (p>0.2 for all comparisons). Neuronal fraction is defined as before as the mean MAP2ab+ fraction. Note that MAP2ab positive cells are virtually absent within the first 2 days, demonstrating the absence of differentiated neurons; notably, it is within this 48 hour period that $Ca^{2+}$ imaging was performed (FIG. 3A,B). B, Assessment of proliferation, survival, and differentiation during days 8 and 9 in excitation or control conditions, as in A. Note the appearance of MAP2ab-positive cells by this timepoint, with a significant increase in the excitation condition. However, again measures of survival, death, and proliferation were unchanged. C, Time course of NeuroD expression (measured by rtPCR as with HES1 and Id2) reveals a persistent elevation caused by excitation (K); Each sample was tested in four replicates, and similar results were observed in two experiments. D, Left: The NeuroD increase was blocked by the $Ca^{2+}$ channel antagonists and not seen in the polyornithine/laminin condition without fixed hippocampal cellular substrate that is incompatible with neurogenesis ("no substrate"). Dotted line represents initial control NeuroD level. Right: No excitation-neurogenesis coupling occurs in the substrate environment that does not permit activity-dependent NeuroD induction (pooled data from 3 independent experiments). Dotted line indicates control unstimulated neuronal fraction with hippocampal substrate.

This increased neuron production was not due to a nonspecific increase in the number of all cells; rather, it was due to an increase in the fraction of the NPCs that became neurons (FIG. 2B). Direct application of the excitatory neurotransmitter glutamate also gave rise to an increase in the fraction of NPCs becoming neurons (FIG. 2B), indicating that the increased neurogenesis was independent of the method of excitation. This effect was not simply on the rate or extent of differentiation measured by MAP2ab expression in the neurons, since the neuronal population did not display an increase in their levels of MAP2ab expression depending on the experimental condition (FIG. 2C, D). Similarly, cells scored as non-neuronal NPC progeny did not exhibit any difference in MAP2ab expression between the different experimental conditions, maintaining a consistently low level of background staining. Excitation moreover did not detectably affect adult NPC progeny proliferation, survival or apoptosis under these conditions (see FIG. 6), indicating that excitation favors adoption of the neuronal phenotype (FIG. 2B, D).

Additional measures confirmed the finding that excitation increased the fraction of adult NPCs that became neurons. Expression of the neuron-specific protein Dcx (FIG. 2E), which is structurally and functionally distinct from MAP2ab, was increased by the depolarization treatment and correlated with MAP2ab expression (FIG. 2E, F). Furthermore, excitation with glutamate or depolarization caused an increase in the fraction of adult NPCs that received functional excitatory synaptic connections, determined electrophysiologically with whole-cell patch clamp recording (FIG. 2G, H). This is a key functional measure that indicates an increase in the fraction of cells adopting authentic neuronal characteristics. We also tested whether the observed adult excitation-neurogenesis coupling was generalizable to other NPC preparations by examining an independently derived early-passage adult hippocampal NPC population (RH-1). Excitatory stimuli also promoted neurogenesis in this line as evidenced by the increased proportion of cells with MAP2ab expression. Thus the results from several independent assays and examination of two independent cell lines indicate that excitatory stimuli favor the production of fully functional neurons from proliferating adult NPCs.

Excitation acts directly on adult hippocampal NPCs. The preceding data address the central question of whether excitation increases or decreases neuron production from adult hippocampal NPCs and that stably active neural networks could adaptively respond by inserting new neurons. However, a key mechanistic question is left unanswered. Is the impact of excitation directly on the NPCs, or indirectly on the surrounding mature hippocampal cells?

Figure 3:
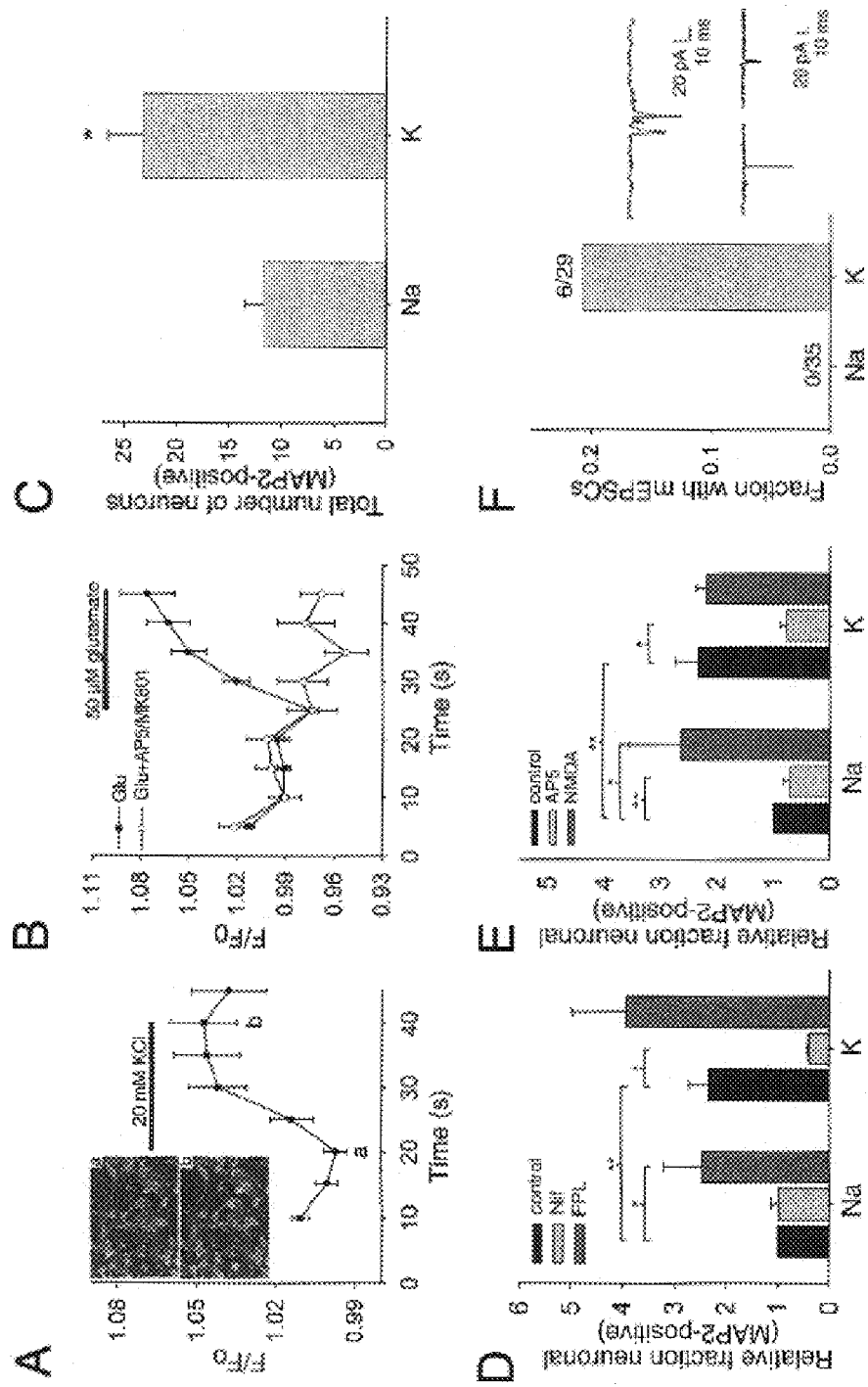
FIG. 3A-3F. Excitation acts directly on adult hippocampal NPCs. A, Depolarization with KCl causes elevations of $[Ca^{2+}]_i$, in proliferating adult-derived NPCs grown on a fixed substrate of hippocampal cultures. Shown is x-Rhod-1 fluorescence expressed as $F/F_0$; increased fluorescence demonstrates elevated $[Ca^{2+}]_i$, which is superimposed on slow photobleaching of the indicator. Mean values of all loaded cells are shown (n=50 cells). Pseudocolor images of the field of cells are shown in the inset at timepoints corresponding to a and b. Warmer (longer wavelength) colors correspond to higher levels of $[Ca^{2+}]_i$. B, $[Ca^{2+}]_i$ response to applied glutamate measured with x-Rhod-1 (n=73); response is blocked by the NMDA receptor antagonists 50 μM AP5/10 μM MK-801 (n=17). C, As in the living coculture condition, total neuron number in 10 randomly selected fields was increased by excitation (n=9, p<0.05). D, Adult-derived NPCs cultured on a fixed hippocampal substrate display robust excitation-neurogenesis coupling (n=7 independent experiments). Bidirectional changes in neurogenesis result from application of $Ca_v1.2/1.3$ channel agonist (FPL64176, 5 μM) or antagonist (nifedipine, 10 μM). E, Bidirectional changes in neurogenesis also result from application of NMDA receptor agonist (NMDA, 50 μM) or antagonist (D-AP5, 50 μM). F, Excitation enhances frequency of synaptic connectivity between NPCs plated on the fixed hippocampal substrate or with conditioned medium from hippocampal cells (light fixation: 0/23 Na, 4/17 K; hippocampal conditioned medium: 0/12 Na, 2/12 K). Traces on the right show sample mEPSCs.

To answer this question, we employed an intervention not possible in vivo. Instead of the living hippocampal coculture environment, we used an ethanol-fixed and extensively washed hippocampal culture as substrate; this is a setting that maintains an environment permissive for neurogenesis, but in which the only living cells are the adult NPCs. Under these conditions, we found that proliferating NPCs themselves responded to excitatory stimuli (depolarization or glutamate) with elevations in intracellular $Ca^{2+}$ (measured with the visible $Ca^{2+}$-sensitive dye X-rhod-1; FIG. 3A,B), indicating expression of responsive $Ca^{2+}$ signaling within the proliferating NPC population. 44 of 73 cells showed an increase with glutamate, and 39 of 50 with depolarization; the actual number of responders is likely higher, as small juxtamembrane calcium elevations on the sub-micron scale (not detectable by imaging) couple robustly to intracellular signaling processes. If this intrinsic $Ca^{2+}$ channel signaling contributes to neurogenesis, then stimulation of these cells grown on the fixed coculture substrate should still enhance neurogenesis. Indeed, we found that both the total number of new neurons (FIG. 3C) and the fraction of MAP2ab-positive cells (FIG. 3D; black bars) were enhanced by depolarization, just as in the living coculture condition. Functional synaptic connectivity between the cells themselves was also enhanced, evidenced by the increased occurrence of spontaneous synaptic currents (FIG. 3F). As the only living cells in the cultures are the NPCs, these data formally demonstrate that excitation acts directly on the actively proliferating NPCs to promote neurogenesis.

How exactly does the excitation influence the NPCs? Excitation by depolarization could act through voltage-activated $Ca^{2+}$ ($Ca_v$) channels, which play a variety of roles in mediating neuronal responses. While $Ca_v2.1$ (N-type) and $Ca_v2.2$ (P/Q-type) $Ca^{2+}$ channels play critical roles in neuronal synaptic transmission, $Ca_v1.2/1.3$ (L-type) $Ca^{2+}$ channels may be implicated in neuronal synaptic plasticity and survival and play a unique and privileged role among the various voltage-sensitive $Ca^{2+}$ channel types in non-synaptic membrane-to-nucleus signaling that modulates activity-dependent gene expression programs (Deisseroth et al. (1998) Nature 392, 198-202).

We explored this issue by employing potent and selective antagonists in the fixed-substrate environment. We found that the peptide $Ca_v2.1/2.2$ channel antagonist ω-Ctx-MVIIC did not inhibit neurogenesis, while the dihydropyridine $Ca_v1.2/1.3$ channel antagonist nifedipine completely blocked excitation-induced neurogenesis (FIG. 3D; light gray bars). We next made use of the $Ca_v1.2/1.3$ channel agonist FPL 64176 as the only external stimulus and conversely observed an enhancement of neurogenesis (FIG. 3D; dark gray bars), demonstrating that $Ca_v1.2/1.3$ channel activation on NPCs is sufficient to promote their neurogenesis.

Certain functions of $Ca_v1.2/1.3$ channels can also be served by NMDA receptors; the two channel types often provide overlapping effects, likely due to a common ability to recruit calmodulin signaling. To test the contribution of NMDA receptors to excitation-neurogenesis coupling under controlled conditions in vitro, we applied the specific NMDA receptor antagonist D-AP5, which inhibited both basal neurogenesis and the enhanced neurogenesis elicited by $K^+$ treatment. Conversely, the specific NMDA receptor agonist NMDA elicited a significant increase in neurogenesis (FIG. 3E).

These experiments, in an environment where no other living cells are present, demonstrate that multiple activity-sensing $Ca^{2+}$ influx pathways are present and functioning on proliferating adult NPCs, and that activation of these pathways promotes neurogenesis. Furthermore this effect does not depend on indirect activity-dependent signals acting via mature neurons or glia. Therefore, proliferating NPCs themselves can act as the signal detection and processing elements mediating adult excitation-neurogenesis coupling.

Immediate impact of excitation on proliferating NPCs. By design, excitation stimuli were applied to the proliferative NPCs concurrently with conditions permitting differentiation, to mimic the hypothesized in vivo situation in which proliferating progenitors are exposed to network activity and exit the cell cycle. We next explored possible mechanisms by which the excitatory stimuli might act, considering first whether excitation acts immediately (on the proliferating progenitors) or in a delayed fashion (for example on cells that have exited the cell cycle and have started to differentiate into neurons).

Figure 4:
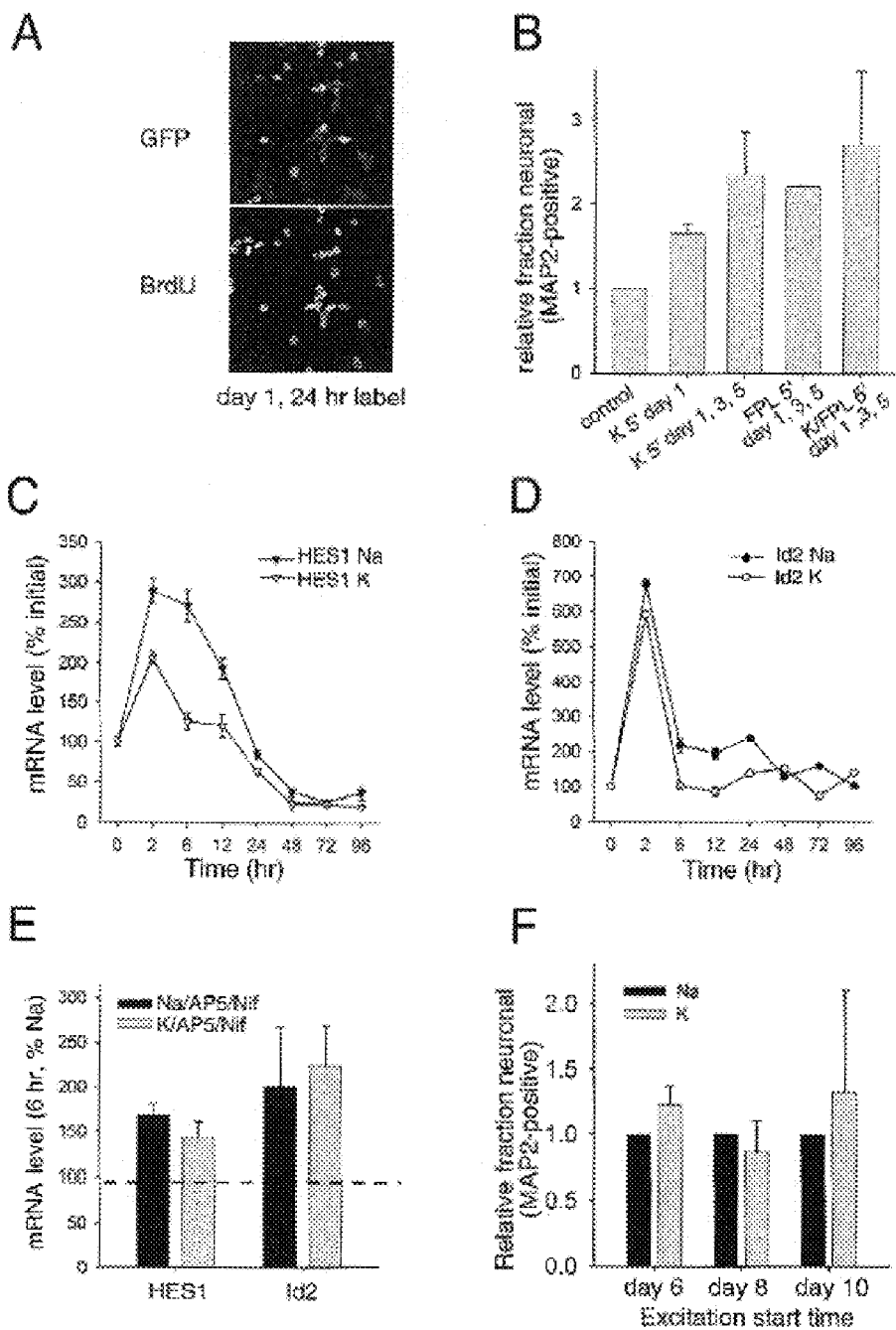
FIG. 4A-4F. Immediate impact of excitation on proliferating NPCs. A, Example of BrdU-labeled cells indicating that excitatory stimuli are applied to proliferating cells; >90% of the NPCs were BrdU+ after a 24 hr label beginning on day 1 when excitation stimuli and conditions permitting neuronal differentiation are applied. B, Brief, spaced excitatory stimuli robustly enhance neurogenesis. When given as a single 5 min pulse on day 1, direct depolarization of the proliferating cells was sufficient for significant excitation-neurogenesis coupling (n=5; p<0.05). Three 5 min pulses spaced every other day (day 1, 3, and 5 after substrate plating and proliferative stimulation) were also effective when given as depolarization (K), direct $Ca_v1.2/1.3$ channel activation with FPL 64176 (FPL), or the combination (K/FPL). C, Immediate bHLH gene response to excitation. Proliferating NPCs were stimulated at the usual time (on day 1 after plating on fixed substrate in mitogens) along with the medium permissive of neuronal differentiation. Excitation (K) was supplemented with FPL 64176 as in FIG. 3. HES1 showed a markedly inhibited profile over the first 1-2 days in the excited samples. All values were normalized to GAPDH transcript levels, and values shown are percent of initial (t=0) values. Each sample was tested in five replicates, and similar results were observed in three independent experiments. D, Id2 likewise was inhibited by excitation, although first effects were not clearly apparent until 6 hr. E, Level of bHLH gene expression at the 6 hr timepoint in the presence of $Ca^{2+}$ channel antagonists. Dashed line corresponds to the unstimulated (Na)/no drug condition for each gene. AP5/nifedipine treatment drives gene expression in the opposite direction as excitation (compare this increase with the decrease in the anti-neuronal fate genes seen at 6 hr in C,D), and also blocks excitation-induced changes in the bHLH genes. F, Excitation applied to postmitotic cells does not give rise to excitation-neurogenesis coupling; depolarization was initiated after full cell-cyle withdrawal on day 6, 8, or 10 and phenotype was assayed on day 14 (n=3; p>0.2 for all 3 conditions).

To determine whether the excitatory stimuli were sensed by proliferative or post-mitotic cells, the cells were labeled with BrdU for 24 hr beginning one day after plating on fixed substrate (starting at the time when excitatory stimuli are applied), then fixed and evaluated for BrdU incorporation. Nearly the entire population (>90%) of NPCs plated on the fixed substrate were rapidly proliferating and labeled with BrdU within this period, when excitatory stimuli are applied (FIG. 4A). We found virtually no neuronal MAP2ab staining at this time point. Moreover, it is these rapidly proliferating NPCs that respond to excitatory stimuli with increased neurogenesis, since even a single brief 5 min stimulus pulse applied at the beginning of this 24 hour BrdU labeling period (during which >90% of the cells are rapidly dividing) elicited significant excitation-neurogenesis coupling (FIG. 4B). Conversely, all neurogenic effects were abolished when the antimitotic agent FUDR was added at this time; under these conditions, more than 95% of all cells were killed, confirming the high mitotic index within cells responding to even brief excitation stimuli. These results demonstrate that brief excitation applied to actively proliferating NPCs is sufficient for excitation-neurogenesis coupling. We also found that 5 minute spaced pulses of depolarization or the $Ca_v1.2/1.3$ channel agonist FPL 64176 on days 1, 3 and 5 enhanced neurogenesis to a similar extent as continuous excitatory stimulation (FIG. 4B), indicating that even brief bouts of excitation are sufficient to strongly drive excitation-neurogenesis coupling via activity-sensitive $Ca^{2+}$ channels within the proliferative NPC population.

The long-lasting effects of brief stimuli indicated that excitation might lead to alterations in transcriptional activities in dividing cells that could modulate stable changes in progeny phenotype. To begin to characterize how proliferating NPCs respond to excitation, we explored the expression dynamics of transcription factors that influence cell phenotype by using real-time rtPCR, again in the fixed-substrate environment to ensure that any observed changes in gene expression must have occurred in the proliferating NPCs. Specifically, we tracked the expression of the mammalian hairy/Enhancer of split homologs HES1 and HES5 (basic helix-loop-helix or bHLH genes which inhibit the neuronal phenotype in proliferating progenitors), the bHLH gene Id2 (which also inhibits development of the neuronal phenotype), and mammalian acheate-scute homolog-1 (MASH1, a multifunctional bHLH gene which can modulate neuron production and is known to modulate HES1/HES5 expression in proliferating progenitors). Under the same conditions as those in FIG. 3, we measured the transcript levels of these genes over the first 96 hr following differentiation under a range of conditions, including the presence or absence of excitation and the presence or absence of channel blockers (FIG. 4C-E).

Excitation provoked a rapid transcriptional modulation of HES1 and Id2 when applied as usual to the proliferating NPCs at day 1, after the first 24 hr of substrate attachment (FIG. 4C,D). Both of these anti-neuronal phenotype genes were depressed rapidly (over 2-6 hr) in the excited sample compared to controls, with a time course lasting ~24 hr (2 hr to 96 hr timepoints shown). Relatively little change was seen in MASH1 and HES5, and little difference was observed by 24 hr after initiation of the excitation in any genes, indicating that the response in these phenotype-determining genes occurs soon after the initiation of the excitatory stimulation and during the period where virtually all cells are still proliferating (FIG. 4A).

We next examined the effects of applying antagonists of $Ca_v1.2/1.3$ channels and NMDA receptors and found that conversely this caused a relative increase in the expression of these anti-neuronal phenotype genes (FIG. 4E). Furthermore, these same antagonists abolished the changes in gene expression caused by excitation (FIG. 4E). These results demonstrate that $Ca^{2+}$ influx through NMDA receptors and $Ca_v1.2/1.3$ channels expressed on the proliferating NPCs rapidly couples to relevant downstream nuclear signaling pathways.

Finally, to determine if any residual neurogenic effects of excitation occur late (after cell-cycle exit), we delayed application of excitatory stimuli until after the cells had exited the cell cycle under differentiating conditions. Depolarization in these post-mitotic cells had no significant effect on the abundance of new neurons (FIG. 4F). Similarly, delayed application of D-AP5 on day 5 did not prevent excitation-neurogenesis coupling (2.76±0.95-fold neurogenesis enhancement, n=7 independent experiments, versus 2.22±0.25-fold enhancement in control, n=5 experiments; p>0.5). Taken together, these data demonstrate that the impact of excitation is immediate and induces a specific gene expression pattern in the proliferating NPCs.

Figure 5:
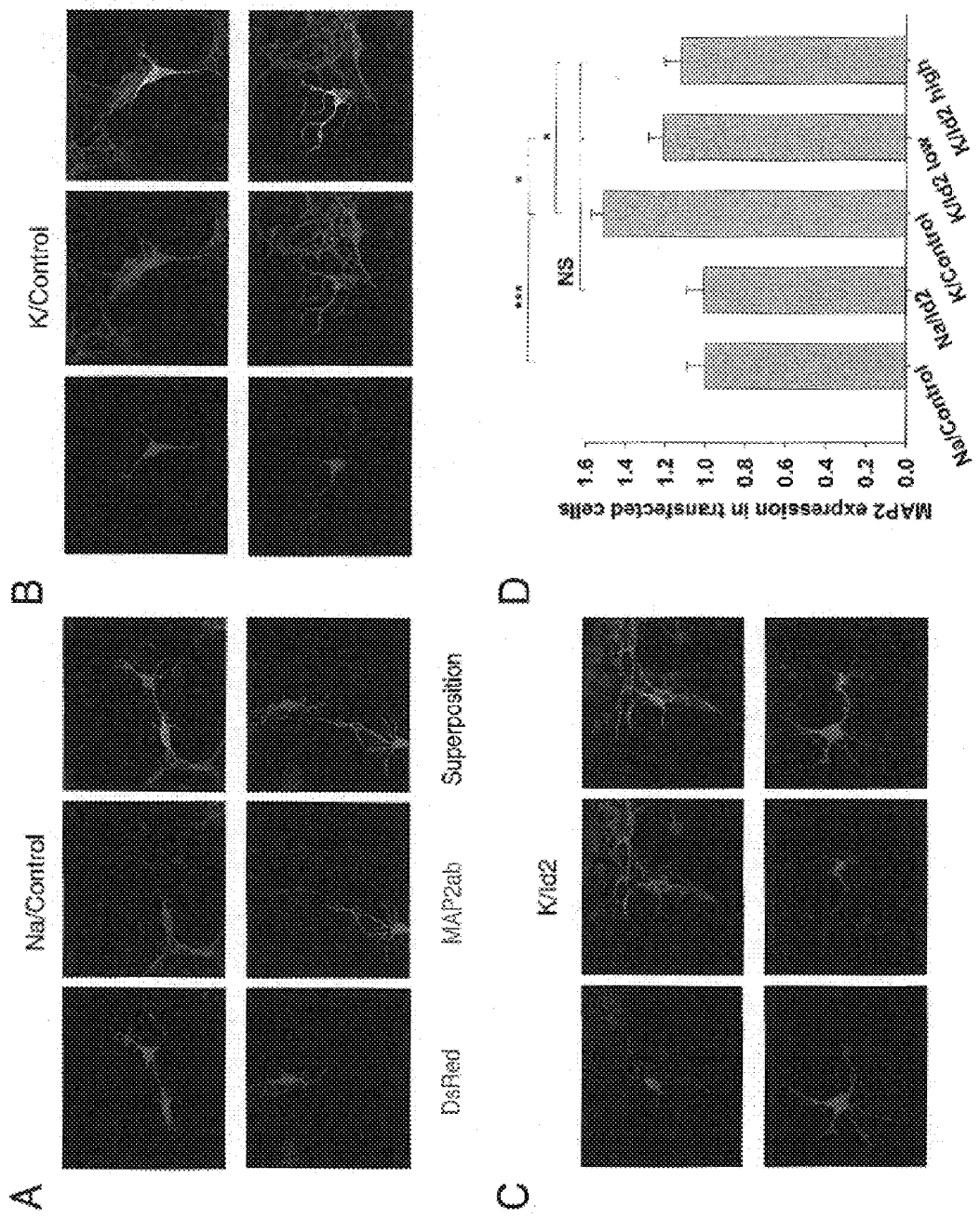
FIG. 5A-5D. Constitutive Id2 expression prevents excitation-neurogenesis coupling. A, Two representative fields of cells under basal excitation conditions (Na) and control plasmid transfection (Control). Left panels show DsRed cotransfection marker (red), middle panels show MAP2ab expression (green), and right panels show the conjunction (yellow) in superposition. B, Two representative fields of cells under stimulated excitation conditions (K) and control plasmid transfection (Control). C, Two representative fields of cells under excitation conditions (K) and constitutive Id2 plasmid transfection (Id2). D, Summary graph showing that the increased neuronal phenotype expression associated with excitation in control transfections (Na/Control, n=70 cells vs K/Control, n=75 cells; p<0.001) was largely blocked in the presence of constitutive Id2. Each condition was applied to three separate coverslips, and results of different doses of the Id2 plasmid in two parallel experiments gave similar results (Id2 low=0.4 µg/well, Id2 high=1.8 µg/well (K/Control vs K/Id2 low, n=46 cells, p=0.033; K/Control vs K/Id2 high, n=36 cells, p=0.018). The K/Id2 conditions were not significantly different from Na/Id2 (Na/Id2 vs K/Id2 low, p=0.068; Na/Id2 vs K/Id2 high, p=0.228). All values were normalized to the Na/Control condition. Basal neuron production was not affected by Id2 (Na/Control vs Na/Id2, n=87 cells, p=0.48).

Constitutive Id2 expression prevents excitation-neurogenesis coupling. If activity-dependent downregulation of a bHLH transcription factor is involved in increasing neurogenesis, then preventing this regulation should inhibit the excitation-neurogenesis coupling. We reasoned that manipulation of Id2 would be likely to reveal mechanistic information, since 1) Id2 is a broadly acting dominant negative regulator of many proneural bHLH transcription factors, and 2) activity-dependent downregulation of Id2 was one of the strongest effects we observed. Specifically, we predicted that if excitation-coupled neurogenesis is dependent, at least in part, on Id2 downregulation, then expression of Id2 from a constitutive promoter should inhibit excitation-neurogenesis coupling. Indeed, in NPC progeny identified by cotransfected DsRed, the excitation-induced increase in neurogenesis (FIG. 5A,B) was largely blocked by constitutive expression of Id2 (FIG. 5C,D). Basal neuron production, however, was not affected (FIG. 5D). These results provide further support for a role of excitation in altering precursor cell fate via a traditional proneural bHLH network regulated by membrane depolarization.

Excitation induces NeuroD, a regulator of neuronal differentiation, in proliferating NPCs. Although depolarization and $Ca^{2+}$-dependent intracellular signaling can in various contexts modulate cell death, proliferation, or survival, we found no significant effect of the mild depolarization used here on apoptosis, proliferation, or net survival of NPC progeny at any time point (using TUNEL labeling, BrdU labeling, and total cell counts respectively measured throughout the experiment, FIG. 6A,B; see figure legend for raw data). For example, total cell counts from 20 random fields corresponding to the experiment displayed in FIG. 6B yielded 52±18 cells in the control condition and 48±7.7 cells in the excitation condition (three independent experiments; p=0.84). Together with the BrdU and TUNEL data, these results demonstrate that excitation by depolarization does not significantly change the proliferative rate, proliferative fraction, survival, or death of the adult NPC progeny.

To further examine whether changes in proliferation or survival are necessary for the immediate proneural impact of excitation, we measured the expression of NeuroD. NeuroD is a downstream regulator of neuronal differentiation which controls expression of a range of genes required for mature neuronal functioning, including structural proteins and ion channels, and coordinates terminal differentiation in dentate gyrus granule cells. Although a great number of bHLH genes interact in intricate and highly redundant ways to control cell fate, if the net transcriptional effects caused by excitation of proliferating NPCs is to rapidly favor commitment to the neuronal phenotype, we predicted that this commitment would be signaled by a relative increase in expression of NeuroD after excitation. Indeed, unlike the anti-neuronal fate bHLH genes, NeuroD expression was rapidly (within 2-6 hours) increased by excitation in the NPCs (FIG. 6C). While excitation-induced decreases in HES1 and Id2 were transient (FIG. 4C,D), the excitation-induced increase in NeuroD expression remained elevated for 96 hours, befitting a gene required for neuronal function (FIG. 6C).

Consistent with the $Ca^{2+}$ channel dependence of excitation-neurogenesis coupling, the NeuroD increase was blocked by the same $Ca^{2+}$ channel antagonists (FIG. 6D). Furthermore, this downstream gene expression response was not seen in NPCs grown in the absence of fixed hippocampal substrate, an environment incompatible with neurogenesis (FIG. 6D; NPCs were plated onto polyornithine/laminin substrate as in Song et al., 2002, but otherwise treated identically). Together, these data demonstrate that, in proliferating adult NPCs, excitation induces a gene expression pattern consistent with neuronal differentiation. The rapidity of the gene expression response further demonstrates that no changes in proliferation or survival are necessary to observe the immediate impact of excitation.

Figure 7:
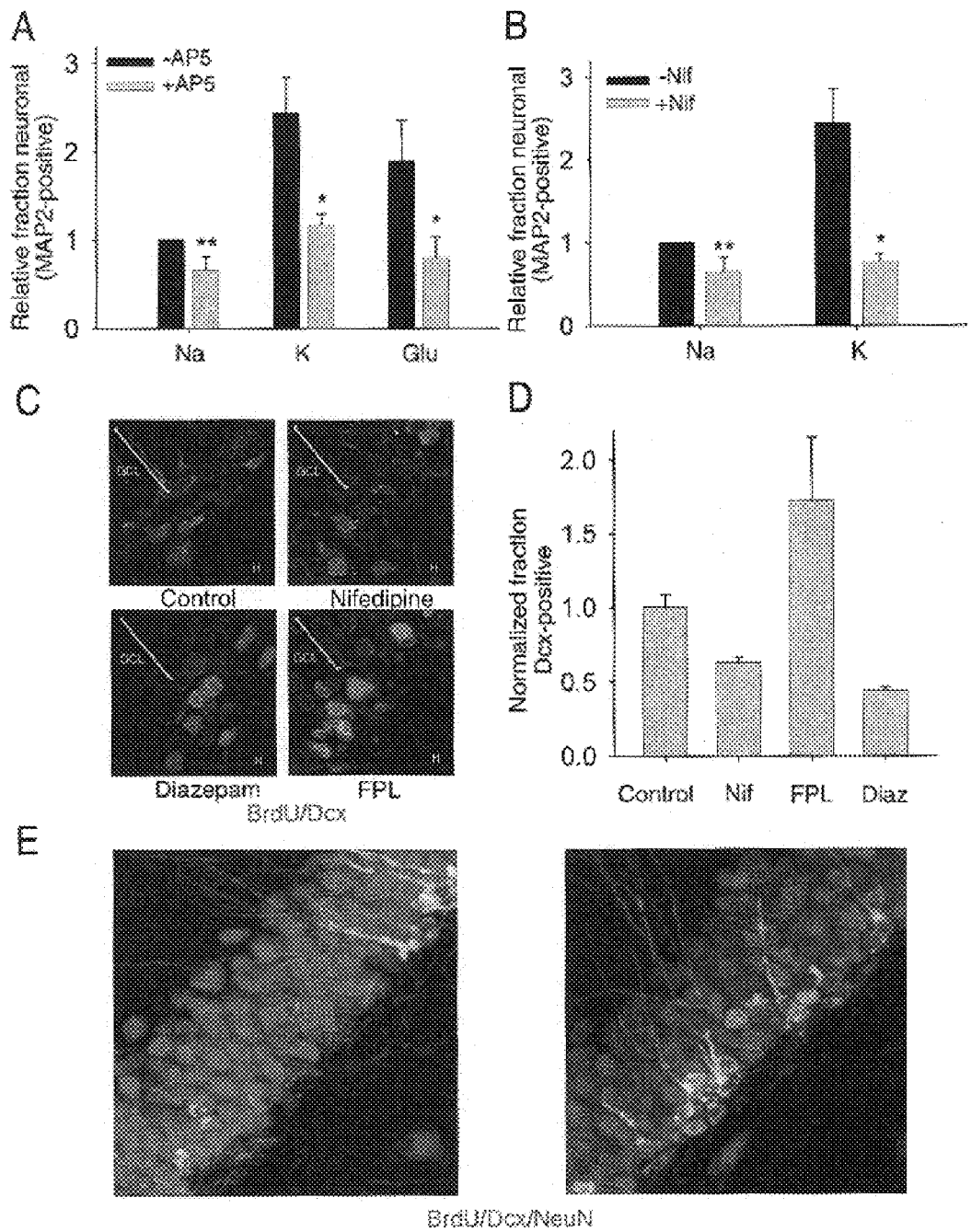
FIG. 7A-7E. $Ca^{2+}$ channel modulators and activity influence neurogenesis in intact systems. A, We employed the living coculture model, as in FIG. 2. Inhibition of NMDA receptors with D-AP5 (50 µM) blocked excitation-induced neurogenesis, via either depolarization or glutamate application. Depolarization (K), n=6 experiments; glutamate (Glu), n=3 experiments. B, The $Ca_v1.2/1.3$ antagonist nifedipine also inhibited basal and excitation-induced neurogenesis (n=3 experiments per condition). Drugs were provided with the differentiation medium in conjunction with the stimuli as before. C, Modulation of $Ca_v1.2/1.3$ channels in vivo significantly influences neurogenesis. For 1 week, adult rats received daily injections of BrdU (50 mg/kg) and either vehicle, nifedipine, FPL 64176, or diazepam (all at 4 mg/kg) as indicated, followed by perfusion and staining for Dcx (red) and BrdU (green); conjunction of the two is shown as yellow. Phenotype of newborn cells was assessed by confocal microscopy with full z-axis analysis. We also observed a trend toward an increased fraction of astroglial and oligodendroglial progeny in the conditions that inhibited neurogenesis (for astroglial phenotype: GFAP/BrdU double-positive cells were 42.7% in control, 58.8% in nifedipine, and 58.5% in diazepam; for oligodendroglial phenotype: NG2/BrdU double-positive cells were 1.4% in control, 3.5% in nifedipine, and 4.7% in diazepam), though these changes were not statistically significant. D, Summary graph of $Ca^{2+}$ channel modulation results. 3 adult female rats were used per condition, with plotted values normalized to control neuronal fraction of 35.3% and representing the fraction of cells among those proliferating during the experimental period (BrdU+) which came to express the early neuronal phenotype (Dcx+). E, $Ca_v1.2/1.3$ channel stimulation causes stable neurogenesis. Rats were treated with BrdU/BayK 8644 (right, n=3) or BrdU/vehicle (left, n=4) for 1 week to label newborn cells in the context of $Ca_v1.2/1.3$ channel stimulation, then allowed to live for 30 days prior to sacrifice. Panels show examples of merged confocal z-stacks of triple labeling for BrdU/NeuN/Dcx. Many of the newborn neurons have migrated into the mature granule cell layer; yellow nuclei in both panels reveal BrdU/NeuN costaining within the GCL (array of red nuclei). Neuronal fraction in BayK was increased to 120%±11% of control (p<0.05), and total BrdU+ cells per hippocampus (subgranular zone and hilus) measured with unbiased stereology increased from 7785±1282 in control to 19633±2677 in Bay K (2.5-fold increase, p<0.005).

$Ca^{2+}$ channels and activity influence neurogenesis in intact systems. The use of an in vitro culture preparation with a fixed substrate permitted a rigorous demonstration of the direct effects of excitation on actively proliferating NPCs. It was important, however, to test whether excitatory stimuli could have the same effects on neurogenesis in more intact systems. Therefore, we next performed experiments using the living coculture model (as in FIG. 2). In this setting, both direct depolarization with $K^+$ and application of glutamate still gave rise to increased neurogenesis, which was blocked by the selective NMDA receptor antagonist D-AP5 (FIG. 7A). Similarly, the selective $Ca_v1.2/1.3$ $Ca^{2+}$ channel antagonist nifedipine blocked depolarization-induced neurogenesis (FIG. 7B). Both nifedipine and D-AP5 exhibited significant inhibition of neurogenesis in the basal (Na) condition as well (FIG. 7A, 7B). These results are consistent with our previous observations that excitation promotes neurogenesis by acting via NMDA receptors and $Ca_v1.2/1.3$ $Ca^{2+}$ channels on the adult NPCs themselves.

If excitation-neurogenesis coupling is operative in vivo and mediates, at least in part, the effects of electrical activity on neuron production, actively dividing cells would need to exist in a cellular niche that exposes them to network activity. The positioning of the NPCs within the axon-rich environment of the hippocampal subgranular zone seems an ideal setting. Here activity-dependent depolarizing mechanisms could directly influence proliferating NPCs, presumably through $Ca_v1.2/1.3$ channels, which as noted above can serve as a potent final common pathway by which electrical signals at the plasma membrane trigger activity-dependent gene expression programs. To test this possibility in vivo, we again employed nifedipine as a potent and selective antagonist of the $Ca_v1.2/1.3$ channels with good CNS penetration. $Ca_v1.2/1.3$ channels do not affect synaptic transmission, whereas other pharmacological modulators such as NMDA receptor antagonists can induce unpredictable activity patterns by dis-inhibiting local circuits.

Consistent with the in vitro results, in vivo administration of nifedipine along with BrdU labeling for 1 week significantly reduced the fraction of newborn cells assuming the neuronal phenotype, observed at the end of the labeling period (n=3; p<0.001; FIG. 7C, 7D). In contrast, direct positive modulation of $Ca_v1.2/1.3$ channels with the agonist FPL 64176 induced a relative increase in the neuronal fraction (FIG. 7C, 7D). $Ca_v1.2/1.3$ channels in vivo presumably respond to native patterns of hippocampal excitatory activity. Therefore, to test the effects of dampening normal endogenous activity patterns on adult neurogenesis, we examined the consequences of chronic administration of diazepam, a long-acting benzodiazepine that has been shown to cause a stable, mild reduction in net hippocampal excitatory activity. In vivo diazepam administration caused a significant reduction in the fraction of BrdU positive cells that assumed a neuronal phenotype (FIG. 7C, 7D; n=3; p<0.002). The results are consistent that activation of $Ca_v1.2/1.3$ channels on adult hippocampal NPCs in vivo promotes neurogenesis.

Many newborn neurons die within the first two weeks in vivo, but behavioral studies of neurogenesis have implicated 2-4 week old newborn neurons in certain aspects of hippocampal function. We therefore asked whether increased neurogenesis associated with $Ca_v1.2/1.3$ channel stimulation could be detected as long as 1 month after the conclusion of the stimulation/BrdU labeling. Employing a milder, well-tolerated agonist of $Ca_v1.2/1.3$ channels for these long-term studies (BayK 8644), we found that increased neurogenesis could be detected 30 days after the last BrdU labeling/channel stimulation treatment; the fraction of newborn cells that were neurons was 120±11% of control (p<0.05; FIG. 7E). Not only was the neuronal fraction increased, reproducing the central in vitro finding, but also a 2.5-fold increase in the total newborn cell number was observed, as illustrated in FIG. 7E. This additional effect serves to even further increase the total number of new stable neurons generated following $Ca_v1.2/1.3$ channel stimulation. Again, these in vivo studies do not allow us to target a particular cell type or isolate a particular mechanism (e.g., proliferation or survival) for the increased neurogenesis. However, taken together, these results extend the findings obtained using the more easily controlled in vitro fixed-substrate preparation to more complicated but more physiological situations, and indicate that the increased neurogenesis is both robust and stable. These data demonstrate that the results obtained with the cultured NPCs are representative of aspects of the behavior of NPCs in vivo.

Functional consequences of excitation-neurogenesis coupling. Using a simple network modeling approach we find that the excitation-neurogenesis coupling relationship described here can underlie beneficial effects of adult neurogenesis in both memory clearance and memory storage.

Models of information storage using simple simulated neural networks have deepened our understanding of normal brain function. Using a simple layered neural network (Graham and Willshaw, (1999), supra.) (FIG. 8A) capable of storing and recalling many patterns of activity, we have asked whether new neurons can be usefully incorporated into mature memory processing networks, and explored the advantages and disadvantages of this process in different activity regimes; addressing the question of how neurogenesis allows the network to adapt to different levels of memory storage demands, which in turn are correlated with the activity level in the network. Activity-dependent neurogenesis may affect the future learning of new memories, or the degradation and clearance of previously stored memories.

Full details of the model are provided above. Briefly, memories (in the form of patterns of neuronal activity) are stored in the network using associative or Hebbian synaptic plasticity rules like those used in the hippocampus (e.g., when two neurons are active at the same time during exposure to an input, the efficacy of the synaptic connection between them is increased). Apart from this hippocampus-like provision, no detailed assumptions about wiring or dynamics were made, as little is known about the functional relevance of these parameters to how information is actually stored in the brain. The network has a simple three-layered structure (FIG. 8A, 8B) and can robustly store many memories in the form of activity patterns. Appropriately patterned output (i.e., memory recall, assessed by inspection of the third layer) is elicited by a patterned test stimulation of the first (input) layer. Many memories can be stored using the network synapses, but highly active networks gradually become "overloaded" and begin to display "noisy" or unreliable recall, as individual synapses attempt to satisfy the requirements of too many memories. Simple networks such as these have been widely used as models for information processing or memory storage.

We compared the function of a control, stable network to a network in which neurogenesis occurs in only the middle layer. We observed two key network behaviors relating to memory clearance and memory storage. First, we found that neurogenesis elicited a more rapid loss or clearance of previously stored old memories (FIG. 8C). To some extent this may be expected, as the synapses of the new neurons have no access to information on the old memories formed before their birth, and the turnover of old neurons coupled with behavior of the new neurons therefore can only degrade the network's ability to recall old memories. This aspect of the model may provide a quantitative framework for understanding how a balance of neuron loss and replacement could be important for clearance of previously stored memories, perhaps especially so in a network that had been very active and is heavily overloaded with old memories.

Secondly, with regard to storage of new memories, we found that the newest memories were recalled at a higher fidelity (compared to the zero-neurogenesis stable case) when neurogenesis was allowed to occur (FIG. 8D), despite the fact that total network size was not allowed to increase. This effect can be intuitively understood from the lack of involvement of new neurons in old memories; in effect, their synapses can be devoted more fully to the newer memories, which are then more accurately stored. Critically, this advantage was dramatically greater in networks that had been more active and had been required to store many memories (FIG. 8D), by comparison with the low activity (low storage rate) networks. This conditional advantage of neurogenesis for memory storage in heavily active networks predicts a monotonically increasing function linking network activity level to the relative benefits of neurogenesis in memory storage (FIG. 8D). Note that this advantage does not depend on a particular mechanism for excitation-neurogenesis coupling.

Importantly, such a relationship was in fact found experimentally in the excitation-neurogenesis coupling characteristics of the adult NPCs (FIG. 8E). Because both NMDA receptors and $Ca_v1.2/1.3$ channels mediate their long-lasting effects through $Ca^{2+}$ flux, we tested the dependence of neurogenesis on $Ca^{2+}$ by varying external $[Ca^{2+}]$ in the setting of depolarization in the fixed coculture substrate condition (FIG. 8E). As external $[Ca^{2+}]$ was increased over a broad range up to 1.8 mM, neurogenesis monotonically increased, indicating that within this range a monotonic relationship with positive slope exists between external $Ca^{2+}$ and the extent of neurogenesis. Since there were no living cells present except for the NPCs, these experiments demonstrate that processing mechanisms within the NPCs themselves can in principle implement the simple rules governing the excitation-neurogenesis coupling that had been predicted from network modeling.

Using an array of approaches, we have explored the coupling of excitation to neurogenesis in proliferating adult-derived NPCs, both in vitro and in vivo. Adult neurogenesis is potently enhanced by excitatory stimuli, and involves $Ca_v1.2/1.3$ channels and NMDA receptors. These $Ca^{2+}$ influx pathways are located on the proliferating NPCs, allowing them to directly sense and process excitatory stimuli. We found no effect of excitation on extent of differentiation in individual cells (measured by extent of MAP2ab expression in the NPC-derived neurons), nor did we observe effects on proliferative rate or fraction, survival, or apoptosis. Instead, excitation increased the fraction of NPC progeny that were neurons, both in vitro and in vivo, and total neuron number was increased as well.

The $Ca^{2+}$ signal in NPCs leads to rapid induction of a proneural gene expression pattern involving the bHLH genes HES1, Id2, and NeuroD, and the resulting cells become fully functional neurons defined by neuronal morphology, expression of neuronal structural proteins (MAP2ab and Doublecortin), expression of neuronal TTX-sensitive voltage gated $Na^+$ channels, and synaptic incorporation into active neural circuits. A monotonically increasing function characterizes excitation-neurogenesis coupling, and incorporation of this relationship into a layered Hebbian neural network evidences surprising advantages for both the clearance of old memories and the storage of new memories. Taken together, these results provide a new framework for further investigation of adult excitation-neurogenesis coupling.

In the hippocampal formation, neural stem cells exist either within the adjacent ventricular zone or within the subgranular zone proper at the margin between the granule cell layer and the hilus, where proliferative activity is most robust. These cells do not express neuronal markers but proliferate and produce dividing progeny that incrementally commit to differentiated fates (such as the neuronal lineage) over successive cell divisions. Native NPC populations in vivo are therefore heterogenous with regard to lineage potential. The functional consequences of coupling excitation to insertion of new neurons for the neural network, however, is independent of which precursor cell types respond to excitation.

$Ca_v1.2/1.3$ channels on adult NPCs potently influenced neurogenesis, as the specific agonists (FPL 64176 and BayK 8644) and antagonist (nifedipine) bidirectionally modulated excitation-neurogenesis coupling in vivo and in vitro. $Ca_v1.2/1.3$ channels are classified among the high voltage-activated (HVA) $Ca^{2+}$ channels and in mature neurons, these channels open primarily in response to the depolarization provided by excitatory synaptic inputs. In proliferating NPCs, which presumably are not synaptically connected, these channels may be activated by a number of other mechanisms. First, $Ca_v1.2/1.3$ channels may be partially open at rest, since NPCs tend to be more depolarized than mature quiescent neurons. Supporting this hypothesis, we found inhibition of neurogenesis by nifedipine even in the resting, non-stimulated condition. The relative resistance to inactivation that characterizes $Ca_v1.2/1.3$ compared to other HVA channels makes them well-suited to this type of chronic signaling. Additional nonsynaptic depolarizing influences may into play in the densely packed in vivo cellular milieu in which NPCs are found. These include depolarizing responses to extracellular $[K^+]$, which increases during bouts of local neuronal activity and depolarizing (ephaptic) responses to voltage changes in active neighboring neurons.

Second, the NPCs could also express depolarizing receptors that can function without classical synaptic contacts. Chief among these possibilities, the NMDA receptor (which passes both $Ca^{2+}$ and $Na^+/K^+$) can have a powerful depolarizing influence and has a very high affinity for glutamate, allowing detection of "ambient" or extrasynaptic glutamate, the levels of which change in response to activity. Indeed, NMDA receptors also were found to be important in excitation-neurogenesis coupling in adult NPCs, as the antagonist D-AP5 and agonists NMDA and glutamate bidirectionally regulated neurogenesis.

Excitation required target cells to be proliferating for effects on neurogenesis to be observed, as excitation provided after cell-cycle exit had no effect on neuron abundance. Conversely, excitation provided as a short (5 min) pulse when NPCs were known to be virtually all actively proliferating sufficed to give rise to significantly increased neurogenesis. These findings led to the question of whether proliferating NPCs could respond to excitation with an appropriate transcriptional response. To address this issue, we used real-time PCR to quantify the effects of excitation on the expression levels of several key bHLH genes in the proliferating adult NPCs. Excitation indeed caused rapid induction of a gene expression pattern characterized by decreases in expression of the anti-neuronal phenotype genes HES1 and Id2 and a rapid and stable increase in the expression of the downstream neuronal differentiation regulator NeuroD. Antagonism of $Ca_v1.2/1.3$ channels and NMDA receptors blocked the excitation-induced responses of all three bHLH genes, providing an independent assay for the ability of $Ca^{2+}$ influx to couple effectively to intracellular signaling pathways in adult NPCs. Evidence for the functional importance of these molecular responses in excitation-neurogenesis coupling was provided by the demonstration that preventing the activity-dependent downregulation of Id2 prevented the normal excitation-induced increase in neurogenesis. $Ca^{2+}$ signaling through $Ca_v1.2/1.3$ channels and NMDA receptors can activate a broad array of rapidly responsive transcription factors, including CREB, NF-ATc4, NFκB, MEF2, c-fos, and others. Moreover, excitation could in principle induce release of autocrine factors from the NPCs themselves leading to recruitment of a host of additional signaling pathways to nuclear transcription factors.

Our findings are consistent with the principle that local cellular environments are important in controlling neurogenesis. Indeed, we found that adult NPCs grown in an environment nonpermissive for neurogenesis were unable to respond to excitation. Cells with neurogenic potential exist elsewhere in the brain as well, including neocortex, but contribute to neurogenesis only in the subventricular zone and the dentate gyrus subgranular zone. However, when cells from non-neurogenic areas are removed and transplanted into neurogenic areas, neuronal progeny result. Our results suggest that one contributing factor to the different neurogenic potential of different brain areas may be differences in the ability of local neuronal activity to induce competence for excitation-neurogenesis coupling in the resident population of NPCs, just as differences in local astroglia can also contribute. This regional variation might be due to local activity itself, physical access of resident NPCs to the local activity, ability of the local environment to induce activity-sensing competence in the NPCs, or factors intrinsic to the resident NPCs themselves.

The enhancement of hippocampal neurogenesis by behavioral stimuli such as environmental enrichment and running may, at least in part, be implemented at the molecular level by excitation-neurogenesis coupling. Notably, running and environmental enrichment increase adult neurogenesis in the hippocampus, but not in the subventricular zone.

Adult excitation-neurogenesis coupling could be a special adaptation with a unique information processing purpose. In the model neural network (FIG. 8), this single phenomenon surprisingly promoted both clearance of old memories and storage of new memories, precisely the two roles to which adult neurogenesis has been experimentally linked. Indeed, the $Ca^{2+}$ influx pathways shown here to be important for excitation-neurogenesis coupling also contribute to synaptic plasticity and presumably stable memory formation in mammals. The existence of excitation-neurogenesis coupling may be particularly important in the hippocampus, a heavily-used locus for temporary memory storage, where frequent memory turnover heightens the need for efficient means of eliminating old memories while reliably storing new memories.

The effect of $Ca_v1.2/1.3$ channel stimulation on the fraction of newborn neurons identified in vitro was also observed in vivo and found to be stable; an additional effect on total newborn cell number was also observed in the in vivo preparation that serves to further increase the impact of $Ca^{2+}$ channel stimulation on the total increase in neurons observed. That $Ca_v1.2/1.3$ excitation robustly promotes neurogenesis ~3-fold from adult NPCs in vivo has important clinical implications, particularly as NPCs can invade regions of damaged brain tissue following stroke, and in some circumstances can contribute to long-range connections and functional recovery. Pharmacological interventions or manipulations of neural activity could enhance the ability of either native or transplanted NPCs to restore function to damaged areas of the CNS.

Electroconvulsive therapy (ECT), as used for treatment of psychiatric and neurological disorders, is particularly intriguing along these lines, involving brief ~1 min induced seizures (global excitatory activity) provided every other day. This therapeutic pattern is similar to the pulse pattern provided in FIG. 4B. ECT can be adapted to specifically promote neurogenesis.

Activity-dependent proliferative bursts in the dentate gyrus can be caused by other clinically relevant phenomena as well, including stroke and seizure, which both cause acutely increased local excitation. The excitation-neurogenesis coupling relationship described here may help guide the neurogenesis observed after such proliferative bursts.

Experimental Procedures

In vivo neurogenesis assays. For in vivo manipulation of neurogenesis, adult 160 g female Fisher rats were injected once per day over a six day period with BrdU (50 mg/kg i.p. in 0.9% saline) along with drug or vehicle control (1% Tween-80/1% ethanol; drug and vehicle injections were over 7 days, initiated one day before the BrdU injections commenced), anaesthetized (0.75 mg/kg acepromazine, 80 mg/kg ketamine and 20 mg/kg xylazine in saline), and sacrificed on the $7^{th}$ or $30^{th}$ day after BrdU initiation by transcardial perfusion with chilled 4% paraformaldehyde in PBS, followed by overnight postfixation via submersion in 4% PFA/PBS. The agents used (BayK 8644, FPL 64176, nifedipine, and diazepam) are highly hydrophobic and chosen to cross the blood-brain barrier, necessitating the use of vehicles for solubilization in the injection; the fraction of BrdU+ cells also staining with Dcx in the control case was 35%. Over this timescale neither vehicle agent has yet been shown to affect neurogenesis in the hippocampus. FPL 64176, nifedipine, and diazepam were all dosed at 4 mg/kg in an injection volume of 1.6 ml, diluted from 50× stocks, and BayK 8644 was dosed at 1 mg/kg. All treatments were well-tolerated with the exception of FPL 64176, as previously reported. Although the low dose used did not lead to overt dystonias, two of the FPL 64176-treated animals died shortly before sacrifice on the $7^{th}$ experimental day. The brains of these two animals were removed and coronally sliced to expose the hippocampus; fixation by 4% PFA/PBS submersion overnight and subsequent staining was quantitatively indistinguishable from the FPL 64176/transcardially perfused condition. For this reason, the milder agonist Bay K8644 was used for the long-term survival studies.

Following fixation, brains were immersed in 30% sucrose/$dH_2O$ for 4 days; 40 µM sections were cut and stored in HistoPrep cryoprotectant prior to staining. Floating sections were rinsed in TBS followed by block for 30 min in 0.3% Triton X-100 and 3% Normal Donkey Serum in TBS (TBS++). Primary antibody staining was conducted in TBS/1% Normal Donkey Serum/0.3% Triton X-100 overnight at 4 degrees C. on a rotary shaker. Primary antibodies used were goat anti-Doublecortin (1:500, Santa Cruz Biotechnology) and rat anti-BrdU (1:500, Accurate). Sections were then rinsed 3× in TBS, followed by overnight incubation in fluorophore-conjugated secondary antibody (1:1000) staining in TBS++. Sections were again rinsed 3× in TBS and postfixed for 10 min at room temperature in 4% PFA/PBS, rinsed 1× in 0.9% saline, denatured for 30 min at 37 degrees C. in 2 M HCl, rinsed in TBS, blocked and stained as above for BrdU, aligned on slides in 50 mM phosphate buffer, partially dried, mounted, and coverslipped in 125 µL polyvinyl alcohol-DABCO. Unbiased stereological analysis with Abercrombie correction was employed to measure total BrdU+ cell number and total hippocampal volume; no significant effects on hippocampal volume were observed.

Adult NPC line derivation and culture. Hippocampus-derived NPCs were isolated from adult rat hippocampi and cultured as previously described. Briefly, adult 6-8 week old female Fisher-344 rats were deeply anesthetized with sodium pentobarbital and were dissected immediately. Hippocampi were enzymatically dissociated with papain (2.5 U/ml; Worthington, Freehold, N.J.)-dispase II (1 U/ml; Boehringer Mannheim, Indianapolis, Ind.)-DNase I (250 U/ml, Worthington) solution. Digested tissue was then washed with DMEM-10% fetal calf serum (FCS) and subsequently mixed with PBS-equilibrated Percoll solution to a final concentration of 35% Percoll. The Percoll solution was made by mixing nine parts of Percoll (Amersham Pharmacia Biotech, Uppsala, Sweden) with one part of 10×PBS. The cell suspension was then fractionated by centrifugation for 10 min at 1000×g. Floating myelin and tissue debris were discarded and the cell pellet re-suspended in 65% Percoll solution and fractionated again by centrifugation for 10 min at 1000× g. The floating neural progenitors were collected, washed free of Percoll, and plated onto poly-L-ornithine/laminin-coated dishes in DMEM/F12 (1:1) containing 10% FCS medium for 24 hrs; then medium was replaced with serum-free growth medium consisting of DMEM/F12 (1:1) supplemented with N2 supplement (Invitrogen, Gaithersburg, Md.) and 20 ng/ml of human recombinant FGF-2 (Peprotech, Rocky Hill, N.J.). Cell lines were labeled via infection with replication deficient GFP-expressing recombinant retrovirus, NIT-GFP (Palmer et al., 1999) or LZRS-CAMut4GFP (Okada et al., 1999). The majority of experiments with HC37 cells transduced with NIT-GFP were conducted at passage number ~25. Cell lines were propagated in DMEM/F12 with 20 ng/ml bFGF, penicillin/streptomycin/amphotericin B (Life Technologies), and N2 supplement (Life Technologies). Plastic tissue culture-treated dishes were coated with 10 µg/ml polyornithine in $dH_2O$ overnight under UV illumination, rinsed 2× with $dH_2O$, recoated with 5 µg/ml mouse laminin (Invitrogen), incubated overnight at 37° C., and frozen for long-term storage at −80° C. Cells were fed every 2-3 days by 75% solution exchange and split 1:4 every 6-7 days after brief trypsinization and centrifugation. Freezing was in DMEM/F12/10% DMSO/BIT supplement (StemCell Technologies), and thawing from storage was in DMEM/F12/BIT.

Hippocampal cell culture. Hippocampi of postnatal day 0 (P0) Sprague-Dawley rats were removed and placed in a dissecting solution containing (in mM): 161 NaCl, 5.0 KCl, 2.9 $CaCl_2$, 5.0 HEPES, and 5.5 glucose, 0.53 $MgSO_4$, and 0.0056 phenol red, pH 7.4. Tissue was treated with papain (20 U/ml) in 10 ml of this solution with additional (in mM) 1.7 cysteine, 1 $CaCl_2$, and 0.5 EDTA for 45 min at 37° C. The digestion was stopped by replacing the solution with 10 ml of MEM/Earle's salts without L-glutamine along with 20 mM glucose, Serum Extender (1:1000), and 10% heat-inactivated fetal bovine serum containing 25 mg of bovine serum albumin (BSA) and 25 mg of trypsin inhibitor. The tissue was triturated in a small volume of this solution with a fire-polished Pasteur pipette, and ~100,000 cells in 1 mL plated per coverslip in 24-well plates. Glass coverslips (pre-washed overnight in HCl followed by several 100% EtOH washes and flame sterilization) were coated overnight at 37° C. with 1:50 Matrigel (Collaborative Biomedical Products, Bedford, Mass.). Cells were plated in culture medium, Neurobasal containing 2× B-27 (Life Technologies) and 2 mM Glutamax-I (Life Technologies). One-half of the medium was replaced with culture medium the next day, giving a final serum concentration of 1.75%. For lightly fixed tissue experiments, stem/progenitor cells were plated after hippocampal cultures at 7 DIV were exposed to 70% EtOH at −20° C. for 30 min, then washed 2× in sterile PBS. The NPCs were plated on the fixed substrate in 25% conditioned medium from the neuron/glia culture and 75% culture medium, as in coculture experiments (see below).

Stem cell coculture. 75% of the medium was removed from each well of the hippocampal cultures and replaced with Neurobasal/B27/penicillin/streptomycin/glutamine (coculture solution) containing the additional mitogens 20 ng/ml VEGF and 20 ng/ml PDGF (both from Peprotech) and rapidly proliferating NPCs (trypsinized from passaging dish, centrifuged, and resuspended). After one day of attachment to substrate, the proliferating stem/progenitor cells were then synchronously subjected to mitogen taper (=day 1); three 75% medium exchanges were carried out every other day with coculture differentiation solution containing 2% fetal bovine serum, 0.5 µM all-trans retinoic acid (prepared freshly on day of use), 10 µM forskolin, and 20 ng/ml NT3. Mitotic inhibitor FUDR (5-fluoro-2'-deoxyuridine) was included with uridine at 0.3 mM unless otherwise indicated at the start of the sixth day post-plating, after cell cycle exit and initiation of differentiation, to allow for long term culture (in some experiments 50 µM D-AP5 (RBI) was also included as noted in the text). Thereafter cultures were supplemented with NT3 to 20 ng/mL every 2-3 days until cocultures were 9-16 days old (control and experimental conditions were always conducted in parallel and therefore were age-matched at all times), at which point neurogenesis assays were performed.

Excitation of NPCs in coculture. Stimuli were started on day 1 along with the initiation of mitogen taper and were included in the three 75% solution exchanges: added 50 µM glutamate, added 16 mM KCl, or added 16 mM NaCl as an osmotic control. As Neurobasal medium already contains 4 mM KCl, the potassium concentration rises to 19.75 mM after the final medium exchange. Divalent cation concentration was maintained constant in external calcium variation experiments by replacement with equimolar magnesium. Nifedipine (RBI) was used at 10 μM and FPL 64176 at 5 μM. Persistent stimuli were used except where noted, to mimic areas of local persistent high activity and to avoid rebound or washoff effects. For brief stimuli, sham medium changes were conducted for control purposes with no neurogenic effect, and medium was fully replaced for the stimulation and removal of stimulation. An advantage of using depolarization for these brief stimuli is that the logarithmic dependence of depolarization on extracellular potassium described by the Nernst equation obviates the need for extensive washing of the stimulated sample prior to reapplication of the control medium.

Electrophysiology. Electrophysiology was carried out essentially as described by (Deisseroth et al. (1996) Neuron 16, 89-101). Whole-cell recordings were obtained with an Axopatch 1D amplifier (Axon Instruments), NIDAQ National Instruments A/D board, and Igor Pro acquisition software. Cells were visualized on an inverted Nikon microscope with mercury arc lamp attachment. Morphologically, the most neuronal GFP+ cells (phase-bright somata with 2-5 primary processes) present in each condition were selected for recording. For miniature EPSC acquisition, cells were held at −70 mV in voltage clamp; for evoking sodium currents cells were held at −70 mV and stepped to −10 mV. The chamber was perfused with Tyrode's solution containing 129 mM NaCl, 5 mM KCl, 2 mM $CaCl_2$, 1 mM $MgCl_2$, 30 mM glucose, 25 mM HEPES, and 10 μM glycine (pH 7.3 and osmolarity 313±2 mOsm). Whole-cell patch electrodes (3-8 MΩ resistance) were filled with a solution containing 110 mM $CsMeSO_4$, 5 mM $MgCl_2$, 10 mM NaCl, 0.6 mM EGTA, 2 mM ATP, 0.2 mM GTP, and 40 mM HEPES (pH 7.2, 295±2 mOsm), unless otherwise noted. TTX (from Calbiochem) at 1 μM was applied and washed via custom designed perfusion pipes positioned by the patched cell.

Immunocytochemistry and transfection. Cells were fixed in 4% formaldehyde (EM Sciences)/PBS for 20-30 min, washed 3×5 min in PBS/0.1 M glycine, permeabilized for 5 min in 0.1% Triton/PBS/3% BSA, washed 3×5 min in PBS/glycine, blocked for 1-2 hr in PBS/3% BSA, and incubated overnight at 4° C. in PBS/3%BSA/primary antibodies. Cells were then washed 3×5 min in PBS, incubated for 1 hr at 37° C. in PBS/3%BSA/secondary antibodies, washed 3×10 min in PBS, and mounted in Fluoromount (Electron Microscopy Sciences). TUNEL staining was performed with Apoptag Red (Serologicals). MAP2ab monoclonal Ab clone AP20 (Sigma) was used at 1:500, Doublecortin Ab (Santa Cruz Biotechnology) at 1:750, BrdU Ab (Accurate) at 1:500, NeuN at 1:4, and secondary Abs from Jackson Immunoresearch at 1:1000. Cotransfections were carried out with Lipofectamine 2000 according to the manufacturer's instructions immediately after NPC plating. The pIRES-EGFP-Id2 plasmid (with CMV promomter) had low GFP expression from this IRES and cotransfection with DsRed (Clontech) was used to identify transfected cells. ~2-5% of the NPCs were transfected, and results shown therefore represent mean MAP2ab levels from all DsRed-positive cells in each condition rather than neuronal fraction obtained from a histogram. As with all experiments, stimulation or control conditions were initiated 24 hr after transfection on Day 1.

Confocal imaging and analysis. Images were acquired on a Zeiss LSM confocal microscope. Random fields containing GFP+ cells were selected for acquisition under GFP excitation without knowledge of experimental condition, and subsequently scanned using laser lines appropriate to excite the fluorophores corresponding to MAP2ab and other antigens. Data were analyzed using Metamorph software from Universal Imaging. MAP2ab or Dcx fluorescence values were obtained for each GFP+ cell by quantifying the mean intensity of the corresponding fluorophore pixels overlying GFP+ pixels; occasional cells were excluded during analysis if they were found to be overlaid with MAP2ab positive processes from other nearby cells. Histograms of resulting values were generated for each experiment and MAP2ab-positivity threshold values for the fractional neurogenesis criterion were identified from the histograms, which show in the unstimulated case (as in FIG. 2) a sufficiently bimodal character allowing a threshold expression level to be set. Mean data from 12 independent experiments conducted with potassium depolarization were used as the reference point for effects of pharmacological interventions in coculture. For evaluation of proliferation and survival effects, daily cell counts as well as TUNEL and BrdU staining were performed in parallel stimulated and unstimulated cultures. BrdU was applied to cultures at 5 μM for 2 hr, and BrdU staining was conducted with a 20-30 min postfixation and subsequent incubation at 37° C. for 20-30 min in 1 N HCl. For $Ca^{2+}$ imaging, x-Rhod-1 AM (Molecular Probes) was loaded at 10 μM for 30 min at 37° C. into cells on the fixed coculture substrate 1-2 days after initiation of mitogen taper. Solutions for resting and stimulated cases corresponded to the differentiation solutions described above, and values shown represent mean somatic x-Rhod-1 fluorescence averaged over all observed cells. 100% of the cells imaged are represented in the averages.

Total RNA isolation, cDNA synthesis, and SYBR Green real-time quantitative RT-PCR. Total RNA was isolated using RNeasy mini kit (Qiagen) and synthesis of cDNA was performed using the SuperScript First-strand Synthesis System for RT-PCR (Invitrogen) following the manufacturers' instructions. Quantitative SYBR Green real time PCR was carried out as described. Briefly, each 25 μl SYBR green reaction consisted of 5 μl of cDNA (50 ng/μl), 12.5 μl of 2× Universal SYBR Green PCR Master Mix (PerkinElmer Life Sciences) and 3.75 μl of 50 nM forward and reverse primers. Optimization was performed for each gene-specific primer prior to the experiment to confirm that 50 nM primer concentrations did not produce nonspecific primer-dimer amplification signal in no-template control tubes. Primer sequences were designed using Primer Express Software. Quantitative RT-PCR was performed on ABI 5700 PCR instrument (PerkinElmer Life Sciences) by using 3-stage program parameters provided by the manufacturer as follows; 2 min at 50° C., 10 min at 95° C., and then 40 cycles of 15 s at 95° C. and 1 min at 60° C. Specificity of the produced amplification product was confirmed by examination of dissociation reaction plots. A distinct single peak indicated that a single DNA sequence was amplified during PCR. In addition, end reaction products were visualized on ethidium bromide-stained 1.4% agarose gels. Appearance of a single band of the correct molecular size confirmed specificity of the PCR. Primers were as follows (F=forward, R=reverse):

| GAPDH F | SEQ ID NO:1 | AAGAGAGAGGCCCTCAGTTGCT |
|---|---|---|
| GAPDH R | SEQ ID NO:2 | TTGTGAGGGAGATGCTCAGTGT |
| MASH1 F | SEQ ID NO:3 | GACAGGCCCTACTGGGAATG |
| MASH1 R | SEQ ID NO:4 | CGTTGTCAAGAAACACTGAAGACA |
| HES1 F | SEQ ID NO:5 | CGGCTTCAGCGAGTGCAT |

-continued

| HES1 R | SEQ ID NO:6 | CGGTGTTAACGCCCTCACA |
| --- | --- | --- |
| HES5 F | SEQ ID NO:7 | GGAGGCGGTGCAGTTCCT |
| HES5 R | SEQ ID NO:8 | GGAGTGGTAAAGCAGCTTCATC |
| ID2 F | SEQ ID NO:9 | ACAACATGAACGACTGCT |
| ID2 R | SEQ ID NO:10 | ATTTCCATCTTGGTCACC |
| NEUROD F | SEQ ID NO:11 | GGACAGACGAGTGCCTCAGTTC |
| NEUROD R | SEQ ID NO:12 | TCATGGCTTCAAGCTCATCCTCCT |

Layered Hebbian neural network. Key characteristics of the model network are noted below. The aim of the model is to explore the effects which excitation-neurogenesis coupling could have on a memory-storage neural network (and not to precisely mimic a particular preparation, though key parallels to hippocampal functioning are included). The network consists of three layers with feedforward, full synaptic connectivity; the output layer activity pattern can be readily conceived of as a stable equilibrium of neuronal activity (according to some theories analogous to the brain state during active remembering), for example with neurons therein capable of persistent activity or participating in simple recurrent connections.

In the results presented there were 500 neurons per layer and neurogenesis with cell turnover permitted only at the middle "dentate gyrus" layer. For modeling clearance of old memories in FIG. 7, turnover fraction was 0.05 for every 50 new patterns stored; for cell death, neurons were selected randomly. As newborn neurons must make functional connections in order to learn, such new neurons were allowed full connectivity to the presynaptic and postsynaptic layers after being born, and allowed to learn subsequent patterns like the other neurons.

Synaptic connections were excitatory and neurons were simple threshold elements with binary activation values $\xi=0$ or 1. As in the hippocampus, pattern representations were sparse; here, fraction of active neurons per pattern or sparsity $(\alpha)=0.02$ in all layers. Synaptic weights J between neurons i and j were set with the standard Hebb rule (Graham and Willshaw, (1999), supra.; Willshaw et al. (1969) Nature 222, 960-962), $J_{ij}=\Sigma(\xi_i^*\xi_j)$, summed over all stored patterns. Activity was propagated through the network in the usual manner, with only the first layer of each stored pattern provided (via the input layer) and activity of the second and third layer determined iteratively as the network attempts to reconstruct the full memory. A given cell j was determined to be active in a reconstructed memory if the incoming activity $\Sigma(\xi_i^*J_{ij})$ summed over all presynaptic neurons i into that cell exceeded a threshold $\theta_j=\alpha_i^*n_i$, where $n_i$ is the total number of neurons in the j−1 layer and $\alpha_1$ is the sparsity of the j−1 layer. Efficacy of memory recall was judged by similarity of the output (third layer) activity pattern compared with the actual stored pattern; each incorrectly active or incorrectly inactive neuron increments the Hamming distance error metric by one unit.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of promoting or inhibiting neurogenesis, the method comprising the step of directly exciting neural progenitor cells in a rat with a therapeutic amount of an agent that directly acts on one or both of voltage-activated gated $Ca^{2+}$ channels or NMDA receptors, wherein when said agent is an agonist of said voltage-activated gated $Ca^{2+}$ channels or NMDA receptors neurogenesis is promoted in said neural progenitor cells, and wherein when said agent is an antagonist of said voltage-activated gated $Ca^{2+}$ channels or NMDA receptors neurogenesis is inhibited in said neural progenitor cells.

2. A method of promoting or inhibiting neurogenesis, the method comprising the step of directly exciting neural progenitor cells with a therapeutic amount of an agent that directly acts on one or both of voltage-activated gated $Ca^{2+}$ channels or NMDA receptors, wherein when said agent is an agonist of said voltage-activated gated $Ca^{2+}$ channels or NMDA receptors neurogenesis is promoted in said neural progenitor cells, and wherein when said agent is an antagonist of said voltage-activated gated $Ca^{2+}$ channels or NMDA receptors neurogenesis is inhibited in said neural progenitor cells wherein said neural progenitor cells are in vitro.

3. The method according to claim 2, wherein said neural progenitor cells are neonatal cells.

4. The method according to claim 2, wherein said neural progenitor cells are adult cells.

5. The method according to claim 2, wherein said agent is the alteration of ionic concentrations in an environment of said neural progenitor cells.

6. A method of promoting neurogenesis in vitro, the method comprising the step of directly exciting neural progenitor cells with a therapeutic amount of an agent that is a specific agonist of $Ca_v1.2/1.3$ channels, wherein generation of neurons from neural progenitor cells is increased in said neural progenitor cells.

7. A method of promoting neurogenesis in vitro, the method comprising the step of directly exciting neural progenitor cells with a therapeutic amount of an agent that is a specific agonist of $Ca_v1.2/1.3$ channels, wherein generation of neurons from neural progenitor cells is increased in said neural progenitor cells, wherein said agonist is selected from FPL 64176 and BAY K-8644.

8. A method of promoting neurogenesis in vitro, the method comprising the step of directly exciting neural progenitor cells with a therapeutic amount of an agent that is a specific agonist of NMDA-R, wherein generation of neurons from neural progenitor cells is increased in said neural progenitor cells.

9. A method of promoting neurogenesis in vitro, the method comprising the step of directly exciting neural progenitor cells with a therapeutic amount of an agent that is a specific agonist of NMDA-R, wherein generation of neurons from neural progenitor cells is increased in said neural progenitor cells, wherein said agonist is selected from GlyT1 inhibitor N[3-(4-fluorophenyl)-3-(4'-phenylphenoxy)propyl]sarcosine (NFPS); NMDA; (R)-(+)-HA-966; glycine; D-serine; (RS)-(Tetrazol-5-yl)glycine, and trans-ACBD.

10. A method of inhibiting neurogenesis in vitro, the method comprising the step of directly exciting neural progenitor cells with a therapeutic amount of an agent that is a specific antagonist of $Ca_v1.2/1.3$ channels, wherein generation of neurons from neural progenitor cells is decreased in said neural progenitor cells.

11. A method of inhibiting neurogenesis in vitro, the method comprising the step of directly exciting neural progenitor cells with a therapeutic amount of an agent that is a specific antagonist of $Ca_v1.2/1.3$ channels, wherein generation of neurons from neural progenitor cells is decreased in said neural progenitor cells, wherein said antagonist is selected from diltiazem, verapamil, nifedipine, nimodipine, and dimemorfan (3-methyl-N-methylmorphinan).

12. A method of inhibiting neurogenesis in vitro, the method comprising the step of directly exciting neural progenitor cells with a therapeutic amount of an agent that is a specific antagonist of NMDA-R, wherein generation of neurons from neural progenitor cells is decreased in said neural progenitor cells.

13. A method of inhibiting neurogenesis in vitro, the method comprising the step of directly exciting neural progenitor cells with a therapeutic amount of an agent that is a specific antagonist of NMDA-R, wherein generation of neurons from neural progenitor cells is decreased in said neural progenitor cells, wherein said antagonist is selected from D-AP5; MK801, memantine, CGP 39551; SDZ 220-581; CGP 78608 hydrochloride; and 5,7-Dichlorokynurenic acid.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: rat

<400> SEQUENCE: 1
aagagagagg ccctcagttg ct                                        22

<210> SEQ ID NO 2
<211> LENGTH: 22
<212> TYPE: DNA
<213> ORGANISM: rat

<400> SEQUENCE: 2
ttgtgaggga gatgctcagt gt                                        22

<210> SEQ ID NO 3
<211> LENGTH: 20

```
<212> TYPE: DNA
<213> ORGANISM: rat

<400> SEQUENCE: 3
gacaggccct actgggaatg                                           20

<210> SEQ ID NO 4
<211> LENGTH: 24
<212> TYPE: DNA
<213> ORGANISM: rat

<400> SEQUENCE: 4
cgttgtcaag aaacactgaa gaca                                      24

<210> SEQ ID NO 5
<211> LENGTH: 18
<212> TYPE: DNA
<213> ORGANISM: rat

<400> SEQUENCE: 5
cggcttcagc gagtgcat                                             18

<210> SEQ ID NO 6
<211> LENGTH: 19
<212> TYPE: DNA
<213> ORGANISM: rat

<400> SEQUENCE: 6
cggtgttaac gccctcaca                                            19

<210> SEQ ID NO 7
<211> LENGTH: 18
<212> TYPE: DNA
<213> ORGANISM: rat

<400> SEQUENCE: 7
ggaggcggtg cagttcct                                             18

<210> SEQ ID NO 8
<211> LENGTH: 22
<212> TYPE: DNA
<213> ORGANISM: rat

<400> SEQUENCE: 8
ggagtggtaa agcagcttca tc                                        22

<210> SEQ ID NO 9
<211> LENGTH: 18
<212> TYPE: DNA
<213> ORGANISM: rat

<400> SEQUENCE: 9
acaacatgaa cgactgct                                             18

<210> SEQ ID NO 10
<211> LENGTH: 18
<212> TYPE: DNA
<213> ORGANISM: rat

<400> SEQUENCE: 10
atttccatct tggtcacc                                             18

<210> SEQ ID NO 11
```

-continued

```
<211> LENGTH: 22
<212> TYPE: DNA
<213> ORGANISM: rat

<400> SEQUENCE: 11
ggacagacga gtgcctcagt tc                                                  22

<210> SEQ ID NO 12
<211> LENGTH: 24
<212> TYPE: DNA
<213> ORGANISM: rat

<400> SEQUENCE: 12
tcatggcttc aagctcatcc tcct                                                24
```